(12) United States Patent
Schmidt et al.

(10) Patent No.: US 6,225,077 B1
(45) Date of Patent: May 1, 2001

(54) METHOD FOR CHARACTERIZING DNA SEQUENCES

(75) Inventors: Günter Schmidt, Cambridge; Andrew Hugin Thompson, Ayr, both of (GB)

(73) Assignee: Brax Genomics Limited, Cambridge (GB)

( * ) Notice: Subject to any disclaimer, the term of this patent is extended or adjusted under 35 U.S.C. 154(b) by 0 days.

(21) Appl. No.: 09/254,023

(22) PCT Filed: Sep. 5, 1997

(86) PCT No.: PCT/GB97/02403

§ 371 Date: Apr. 20, 1999

§ 102(e) Date: Apr. 20, 1999

(87) PCT Pub. No.: WO98/10095

PCT Pub. Date: Mar. 12, 1998

(30) Foreign Application Priority Data

Sep. 5, 1996 (GB) .................................................. 9618544

(51) Int. Cl.[7] .................................................. C12Q 1/44
(52) U.S. Cl. .................................................. 435/19; 435/6
(58) Field of Search ............................................ 435/19, 6

(56) References Cited

U.S. PATENT DOCUMENTS

| | | | |
|---|---|---|---|
| 5,508,169 | 4/1996 | Deugau et al. | 435/6 |
| 5,871,697 | * 2/1999 | Rothberg et al. | 422/68.1 |

FOREIGN PATENT DOCUMENTS

| | | |
|---|---|---|
| 0 735 144 | 10/1996 | (EP) . |
| 0 761 822 | 3/1997 | (EP) . |
| 94 01582 | 1/1994 | (WO) . |
| 96 12039 | 4/1996 | (WO) . |

OTHER PUBLICATIONS

Ko, M.S.H. (1990) Nuc Acids Res. 18(19), 5705–5711.*
Velculescu, V.E. et al., Serial analysis of gene expression, Science, vol. 270, Oct. 20, 1995. pp. 484–487.
Kato, Kikuya, "Description of the entire mRNA population by a 3' and cDNA fragment generated by class IIS restriction enzymes", Nucleic Acids Research, vol. 23, No. 18, 1995, pp. 3685–3690.
Unrau, P, Deugau K.V., "Non–cloning amplification of specific DNA fragments from whole genomic DNA digests using DNA indexers", Gene, vol. 145, 1994, pp. 163–169.
Maier, E. et al., "Hybridization techniques on gridded high density DNA and in situ colony filters based on flourescence detection", Nucleic Acids Research, vol. 22, No. 16, 1994, pp. 3423–3424.

* cited by examiner

*Primary Examiner*—Charles L. Patterson, Jr.
(74) *Attorney, Agent, or Firm*—Burns, Doane, Swecker & Mathis, L.L.P.

(57) ABSTRACT

A method for characterizing cDNA, which comprises: (a) cutting a sample comprising a population of one or more cDNAs or isolated fragments thereof, each having a strand complementary to the 3' poly-A terminus of an mRNA and bearing a tail, with a first sampling endonuclease at a first sampling site of known displacement from a reference site proximal to the tail to generate from each cDNA or isolated fragment thereof a first and second sub-fragment, each comprising a sticky end sequence of predetermined length and unknown sequence, the first sub-fragment bearing the tail; (b) sorting either the first or second sub-fragments into sub-populations according to their sticky end sequence and recording the sticky end sequence of each sub-population as the first sticky end; (c) cutting the sub-fragments of each sub-population with a second sampling endonuclease, which is the same as or different from the first sampling endonuclease, at second sampling site of known displacement from the first sampling site to generate from each sub-fragment a further sub-fragment comprising a second sticky end sequence of predetermined length and unknown sequence; and (d) determining each second sticky end sequence; wherein the aggregate length of the first and second sticky end sequences of each sub-fragment is from 6 to 10; and wherein the sequences and relative positions of the reference site and first and second sticky ends are utilized to characterize said cDNA or cDNAs.

21 Claims, 10 Drawing Sheets

*──GGATG
　　CCTACXXXX ← 1 of 256 possible 4 bp sticky ends

FIG. 3

*──ACCTGCNNNN
　　TGGACGNNNNXXXX

FIG. 4

*────GGATG　　　　　　　　+────GGATG
　────CCTACATGA　　　　　　────CCTACATGT

•────GGATG　　　　　　　　X────GGATG
　────CCTACATGC　　　　　　────CCTACATGG

FIG. 5

METHOD FOR CHARACTERIZING DNA SEQUENCES

FIELD OF THE INVENTION

The present invention relates to a method for characterising DNA, especially CDNA, so that the DNA may be identified, for example, from a population of DNAs. The invention also relates to a method for assaying the DNA.

BACKGROUND OF THE INVENTION

Analysis of complex nucleic acid populations is a common problem in many areas of molecular biology, nowhere more so than in the analysis of patterns of gene expression. Various methods have been developed to allow simultaneous analysis of entire mRNA populations, or their corresponding cDNA populations, to enable us to begin to understand patterns of gene expression in vivo.

The method of "subtractive cloning" (Lee et al, Proc. Nat. Acad. Sci. U.S.A. 88, 2825–2829) allows identification of mRNAs, or rather, their corresponding cDNAs, that are differentially expressed in two related cell types. One can selectively eliminate cDNAs common to two related cell types by hybridising cDNAs from a library derived from one cell type to a large excess of mRNA from a related, but distinct cell type. mRNAs in the second cell type complementary to cDNAs from the first type will form double-stranded hybrids. Various enzymes exist which degrade such ds-hybrids allowing these to be eliminated thus enriching the remaining population in cDNAs unique to the first cell type. This method allows highly specific comparative information about differences in gene expression between related cell types to be derived and has had moderate success in isolating rare cDNAs.

The method of "differential display" (Laing and Pardee, Science 257, 967-971, 1992) sorts mRNAs using PCR primers to amplify selectively specific subsets of an mRNA population. An mRNA population is primed with a general poly-T primer to amplify one strand and a specific primer, of perhaps 10 nucleotides or so to amplify the reverse strand with greater specificity. In this way only mRNAs bearing the second primer sequence are amplified; the longer the second primer the smaller a proportion of the total cDNA population is amplified or any given sequence of that length used. The resultant amplified sub-population can then be cloned for screening or sequencing or the fragments can simply be separated on a sequencing gel. Low copy number mRNAs are less likely to get lost in this sort of scheme in comparison with subtractive cloning, for example, and it is probably more reproducible. Whilst this method is more general than subtractive cloning, time-consuming analysis is required.

The method of "molecular indexing" (PCT/GB93/01452) uses populations of adaptor molecules to hybridise to the ambiguous sticky-ends generated by cleavage of a nucleic acid with a type IIs restriction endonuclease to categorise the cleavage fragments. Using specifically engineered adaptors one can specifically immobilise or amplify or clone specific subsets of fragments in a manner similar to differential display but achieving a greater degree of control. Again, time-consuming analysis is required.

The method of Kato (Nucleic Acids Research 12, 3685–3690, 1995) exemplifies the above molecular indexing approach and effects cDNA population analysis by sorting terminal cDNA fragments into sub-populations followed by selective amplification of specific subsets of cDNA fragments. Sorting is effected by using type IIs restriction endonucleases and adaptors. The adaptors also carry primer sites which in conjunction with general poly-T primers allows selective amplification of terminal cDNA fragments as in differential display. It is possibly more precise than differential display in that it effects greater sorting: only about 100 cDNAs will be present in a given subset and sorting can be related to specific sequence features rather than using primers chosen by trial and error.

The method of "serial analysis of gene expression" (SAGE, Science 270, 484–487. 1995) allows identification of mRNAs, or rather, their corresponding cDNAs, that are expressed in a given cell type. It gives quantitative information about the levels of those cDNAs as well. The process involved isolating a "tag" from every CDNA in a population using adaptors and type IIs restriction endonucleases. A tag is a sample of a cDNA sequence of a fixed number of nucleotides sufficient to identify uniquely that cDNA in the population. Tags are then ligated together and sequenced. The method gives quantitative data on gene expression and will readily identify novel cDNAs. However, the method is extremely time-consuming in view of the large amount of sequencing required.

All of the above methods are relatively laborious and rely upon sequencing by traditional gel methods. Moreover, the methods require amplification by PCR, which is prone to produce artefacts.

Methods involving hybridisation grids, chips and arrays are advantageous in that they avoid gel methods for sequencing and are quantitative. They can be performed entirely in solution, thus are readily automatable. These methods come in two forms. The first involves immobilisation of target nucleic aids to an array of oligonucleotides complementary to the terminal sequences of the target nucleic acid. Immobilisation is followed by partial sequencing of those fragments by a single base method, e.g. using type IIs restriction endonucleases and adaptors. This particular approach is advocated by Brenner in PCT/US95/12678.

The second form involves arrays of oligonucleotides of N bp length. The array carries all $4^N$ possible oligonucleotides at specific points on the grid. Nucleic acids are hybridised as single strands to the array. Detection of hybridisation is achieved by fluorescently labelling each nucleic acid and determining from where on the grid the fluorescence arises, which determines the oligonucleotide to which the nucleic acid has bound. The fluorescent labels also give quantitative information about how much nucleic acid has hybridised to a given oligonucleotide. This information and knowledge of the relative quantities of individual nucleic acids should be sufficient to reconstruct the sequences and quantities of the hybridising population. This approach is advocated by Lehrach in numerous papers and Nucleic Acids Research 22, 3423 contains a recent discussio n. A disadvant age of this approach is that the con struction of large arrays of oligonucleotides is extremely te chnically demanding and expensive.

SUMMARY OF THE INVENTION

The present invention provides a method for characterising cDNA, which comprises:

(a) cutting a sample comprising a population of one or more cDNAs or isolated fragments thereof, each having a strand complementary to the 3' poly-A terminus of an mRNA and bearing a tail, with a first sampling endonuclease at a first sampling site of known displacement from a reference site proximal to the tail to generate from each cDNA or isolated fragment thereof a first and second sub-fragment, each comprising a sticky end sequence of predetermined length and unknown sequence, the first sub-fragment bearing the tail;

(b) sorting either the first or second sub-fragments into sub-populations according to their sticky end sequence and recording the sticky end sequence of each sub-population as the first sticky end;

(c) cutting the sub-fragments in each sub-population with a second sampling endonuclease, which is the same as or different from the first sampling endonuclease, at a second sampling site of known displacement from the first sampling site to generate from each sub-fragment a further sub-fragment comprising a second sticky end sequence of predetermined length and unknown sequence; and (d) determining each second sticky end sequence;

wherein the aggregate length of the first and second sticky end sequences of each sub-fragment is from 6 to 10; and wherein the sequences and relative positions of the reference site and first and second sticky ends characterise the or each cDNA. Optionally, the sample cut with the first sampling endonuclease comprises isolated fragments of the cDNAs produced by cutting a sample comprising a population of one or more cDNAs with a restriction endonuclease and isolating fragments whose restriction site is at the reference site.

This invention involves a process that allows a cDNA population, generated by various means, to be sorted into sub-populations or subsets. The process also allows the identification of individual molecules within a subset and it allows the quantity of those individual molecules to be determined. More specifically this invention is capable of analysing a population of cDNAs derived from a specific cell type to generate a profile of gene expression for that cell. This profile would reveal which cDNAs are present and how much of each is present. From this it should then be possible to determine initial quantities of mRNA present in the cell, possibly by calibrating cDNA quantities against the expression of a known house-keeping gene whose in vivo levels could be determined directly.

It is not necessary to sequence an entire cDNA to identify uniquely its presence; only a short 'signature' of a few base pairs should be sufficient to identify uniquely all cDNAs, given, for example, a total cDNA population of about 80 000 in the human genome. Given also that in the next few years the entire human genome will have been sequenced, it should be possible to use such signatures derived by this process to acquire the entire sequence of the original cDNAs from a sequence database. With the incomplete database that already exists, signatures that return no sequence from the database will probably be novel and this process will readily allow them to be isolated for complete sequencing. If a given signature returns more than one sequence then this process can readily resolve the returned sequence by acquiring further sequence data specifically from the sequence of interest. This is a feature of this process that is of great advantage over other methods such as SAGE.

Velculescu et al, Science 270, 484–487 (1995), have tested human sequences in release version 87 of the GenBank sequence database with every possible 9 bp sequence starting from a particular reference point, their 'anchoring enzyme' cutting site. Their results indicated that with a 9 bp sequence 95.5% of tags corresponded to a unique transcript or highly conserved (>95% sequence identity over at least 250 bp) transcript family. Increasing the number of bp in the tags to 11 bp, used to test the database resulted in only a 6% decrease in the number of tags returning more than 1 sequence from the database.

Statistically, the odds that 2 sequences with the same signature are identical sequences, can be calculated using Bayes' Theorem:

$$P(\text{Identical} | \text{Same Signature}) = \frac{P(\text{Same Signature} | \text{Identical}) \times P(\text{Indentical})}{P(\text{Same Signature})} \quad (1)$$

Where "|" means "given that" and, similarly:

$$P(\text{Not Identical} | \text{Same Signature}) = \frac{P(\text{Same Signature} | \text{Not Identical}) \times P(\text{Not Indentical})}{P(\text{Same Signature})} \quad (2)$$

(1) divided by (2) gives:

$$\text{Posterior Odds Identical} = \frac{P(\text{Same Signature} | \text{Identical}) \times \text{Prior Odds Identical}}{P(\text{Same Signature} | \text{Not Identical})} = 4^N \times \text{Prior Odds Identical}$$

Where N is the number of bases in the signature. $4^N$ clearly will rise very quickly with N. The Prior Odds Identical are the known odds of two random sequences being identical. In terms of a non-redundant sequence database this is actually zero. Thus we have $4^N$ signatures available to search a human sequence database. This analysis assumes equiprobable and spatially uncorrelated bases, which is clearly not true for real sequences. If there is spatial correlation of bases etc., much larger signatures might be necessary but as the analysis of Velculescu et al suggests this is not the case, longer signatures do not give greater resolution of sequences; 9 bp is sufficient as the human genome probably contains of the order of 80 000 sequences of which a large number are closely related, as defined above. An 8 bp signature gives 65536 distinct signatures. For experimental purposes, i.e. for analysing tissue samples this will be enough to resolve the estimated 15000 distinct cDNAs that are expected in the average cell but one might expect that a number of signatures might return more than 1 sequence. These can fortunately be readily resolved by further analysis, as discussed below.

Thus, at least for human cDNAs, the aggregate length of the first and second sticky-end sequences of- each sub-fragment is preferably 8, and conveniently, the length of each sticky end is 4.

cDNAs from species other than humans can also be readily analysed by the process of the present invention. The aggregate length of the first and second sticky-end sequences can be tailored to the size of the cDNA population expected for a particular species with similar optimization procedures as discussed below. The size of the signature may vary depending on the size of the genome to be analysed. More general nucleic acid populations may also be analysed, such as restriction fragments generated from plasmids or small bacterial or viral genomes. Other similarly generated populations could similarly be analysed.

When the restriction endonuclease is used to produce fragments from the cDNAs, it is preferred that the first sampling endonuclease binds to a first recognition site and cuts at the first sampling site at a predetermined displacement from the restriction site of the restriction endonuclease.

Preferably, the first recognition site is provided in a first adaptor oligonucleotide which is hybridised or ligated to the restriction site of the isolated fragments. In this way, the fragments need contain no recognition site for the first sampling endonuclease. Preferably, a low stringency restriction endonuclease is used to generate the cDNA fragments, such as one which recognises a 4 base pair binding site (e.g. NlaIII which cuts at CATG leaving a 4 bp sticky-end). If too large a binding site needs to be recognised, the probability that no recognisable binding site is present in a specific cDNA is too great.

As an alternative to using the restriction endonuclease, the first sampling endonuclease may bind to the reference site and cut at the first sampling site at a predetermined displacement from the reference site. In either arrangement, it is necessary that a reference site be used because this site contributes to the information required to establish each "signature".

The importance of this step should be noted with regard to analysing a population of cDNAs. Cleaving the immobilised cDNAs with the 'reference enzyme' (i.e. the restriction endonuclease or first sampling endonuclease) will leave fragments that are known to be terminated by the reference site that is most 3' on the cDNA. With the purpose of searching a database in mind this greatly reduces the search by starting from the restriction site nearest the 3' terminus (see FIG. 8). It also gives additional spatial information regarding the positions of the 'signature', in that there is a defined spacing between an 8 bp signature, say of two quadrats, and the reference site. There is a lower probability of an 8 bp signature occurring with a given spatial relationship to a defined restriction site than for a given 8 bp sequence to appear at a random position in the whole cDNA or in the genome as a whole. In this way the determinative power of an 8 bp signature is increased so that it is sufficient to identify uniquely all or at least the vast majority of cDNAs.

It is also important to ensure no sampling endonuclease recognition sites are present in the cDNA fragments prior to addition of adaptors bearing the sampling endonuclease recognition site. To avoid this problem the cDNA can be pretreated with the sampling endonuclease before use of the restriction endonuclease or for that matter the sampling endonuclease and restriction endonuclease can be the same enzyme. This will generate fragments with ambiguous sticky-ends. If a different 'reference enzyme' is to be used, the majority of these sticky-ends will be removed by the subsequent cleavage with the 'reference enzyme' as this would be chosen to cut more frequently. Those that remain will be accounted for in the sorting process. This means that there will effectively be two 'reference enzymes' and this must be taken into account in the subsequent database searching by searching for both possible reference. sequences. This might return more sequences for each region of 8 bp of variable sequence, thus use of two reference enzymes would preferably be avoided.

As a preferred alternative, to ensure the sampling endonuclease binds only to occurrences of its recognition sequence within an adaptor rather than to occurrences which may occur in the cDNA, one can synthesise the cDNA with 5-methyl cytosine and use adaptors synthesised with ordinary cytosine nucleotides. As long as one uses a sampling endonuclease that is methylation sensitive, the sampling endonuclease will only bind to occurrences of its recognition sequence in an adaptor.

Preferably, the second sampling endonuclease binds to a second recognition site and cuts at the second sampling site at a predetermined displacement from the first sampling site. In this way, information (in the form of the first and second sticky-end sequences) is derived from first and second sampling sites and, additionally, their displacement from one another and from the reference site is known. Preferably, the first and second sampling endonucleases each comprise a type IIs endonuclease, which may be the same as or different from one another. The second recognition site may be provided in a second adaptor oligonucleotide which is hybridised or ligated to the first sticky-end.

The process of the present invention acquires minimal sequence data so that it is not reliant on excessive sequencing. It does not require traditional gel methods to acquire minimal sequence information. Since the entire process takes place in solution, the steps involved could be performed by a liquid-handling robot; hence this process is highly automatable. Sequence data in an automated system can then be acquired in parallel for the entire cDNA population of a cell.

Mixed nucleic acid population
↓
Sort molecules into subsets
↓
Sample sequence or otherwise characterise molecules within subsets simultaneously The process avoids excessive sequencing using a sampling procedure, above, to generate signatures for each cDNA in a population. The preferred form of these signatures would be:

5'-CATGNNNNNXXXXNNNNNYYYYNNN . . . NNNAAAAAAAA-3'

Reference . . . space . . . Sample 1 . . . space . . . Sample 2 . . . unknown space . . . poly-A tail This sort of signature would preferably be acquired from an immobilised CDNA population but clearly a signature could be acquired from anywhere in a sequence but it must be from the same defined reference point in each sequence to be compared if minimal sequence data is to be usable. The cDNA population is preferably immobilised using the poly-A tail, in bold at 3' terminus, using, for example, a solid phase matrix. The first 4 bp of the signature, in bold, is known, as this corresponds to the reference site which could be from a low stringency ordinary type II restriction endonuclease. This may be used to fragment the cDNA population initially to generate a reference point from which samples are taken to generate unique signature information for every cDNA in a cell. The next 4 bp in bold, are acquired at a known number of bp, which is the same for every cDNA in a population, from the 'reference site' by the 'first sampling endonuclease', which preferably is a type IIs restriction endonuclease. These 4 bp are unknown, but obviously only 256 possibilities exist. These may be determined by pulling out subsets corresponding to each of the possible 4 bp sequences using beads with oligonucleotides complementary to one of the possible sequences as described below for the sorting procedure. The next 4 bp in bold, are again generated at a known. distance, which is the same for every cDNA in a population, from the first sampled sequence possibly by the same type IIs 'sampling enzyme' and may be determined by the 'adaptor cycle', as described below. Thus for every cDNA, we have a known restriction site that is the last one of its kind on the cDNA before the poly-A tail, separated by a known distance from a sample of the cDNA sequence of known length. This sample in turn is separated from the next sample by a known number of bp and the second sample length is again defined.

The sample lengths can be up to 5 bp as determined by the enzymes presently available. The distances between the samples or between the first sample and the reference site can be up to20 bases but the actual distance does not matter except that it must be known.

The restriction endonuclease cutting sequence can be of any length as long as it is a sequence that is recognised by a type IIs restriction endonuclease but practically speaking it must such as to ensure that the enzyme actually cuts every CDNA and that the terminal fragments of the cDNAS that remain are of a reasonable length to sample subsequently with the sampling endonuclease.

Clearly if a nucleic acid population is subjected to cleavage with a restriction endonuclease there will be sticky-ends at both termini of the nucleic acid fragments which in most cases would be different at each end. This would cause problems to this sorting process.

For the purposes of this invention use of mRNA avoids this problem, since the 3' terminus of the UTR of a mRNA is characterised by the presence of a poly-A tail. This can be used to immobilise one terminus of each mRNA present to a matrix with a complementary poly-T oligonucleotide attached to its surface. This ensures only one terminus is exposed to subsequent cleavage by the type IIs restriction enzyme after cDNA synthesis. After restriction all non-immobilised fragments, i.e. those without a poly-A tail are to be washed away leaving only the immobilised terminal fragments. The purpose of this process is to derive sufficient information to identify uniquely each cDNA molecule present in a population. As long as the terminal fragments are of the order of about 10 to20 nucleotides from the termination codon, this should be sufficient to obtain a unique signature for every cDNA, given a maximum total population of about 100 000 cDNAs in the human genome.

Type IIs restriction endonucleases, the 'sampling endonucleases', have the property that they recognise and bind to a specific sequence within a target DNA molecule, but they cut at a defined distance away from that sequence generating single-stranded sticky-ends of known length but unknown sequence at the cleavage termini of the restriction products.

For example, the enzyme fok1, generates an ambiguous (i.e. unknown) sticky-end of 4 bp, 9 bp downstream of its recognition sequence. This ambiguous sticky-end could thus be one of 256 possible 4 bp oligonucleotides (see FIG. 1). Numerous other type IIs restriction endonucleases exist and could be used for this process as discussed below in section on restriction endonucleases. Their binding site can be provided by the adaptors used as shown in FIG. 2, for example.

Numerous type IIs restriction endonucleases exist and could be used as sampling enzymes for this process. Table 1 below gives a list of examples but is by no means comprehensive. A literary review of restriction endonucleases can be found in Roberts, R., J. Nucl. Acids Res. 18, 2351–2365, 1988. New enzymes are discovered at an increasing rate and more up to date listings are recorded in specialist databases such as REBase which is readily accessible on the internet using software packages such as Netscape or Mosaic and is found at the World Wide Web address: http://www.neb.com/rebase/. REBase lists all restriction enzymes as they are discovered and is updated regularly, moreover it lists recognition sequences and isoschizomers of each enzyme and manufacturers and suppliers. The spacing of recognition sites for a given enzyme within an adaptor can be tailored according to requirements and the enzyme's cutting behaviour. (See FIG. 2 above).

TABLE 1

Some typical type IIs restriction endonucleases

| Enzyme Name | Recognition sequence | Cutting site |
|---|---|---|
| Fok1 | GGATG | 9/13 |
| BstFs1 | GGATG | 2/0 |
| SfaNI | GCATC | 5/9 |
| HgaI | GACGC | 5/10 |
| BbvI | GCAGC | 8/12 |

The requirement of the process is the generation of ambiguous sticky-ends at the termini of the nucleic acids being analysed. This could also be achieved by controlled use of 5' to 3' exonucleases. Clearly any method that achieves the creation of such sticky-ends will suffice for the process.

Similarly the low stringency restriction endonuclease is necessary only to cleave each cDNA once, preferably leaving sticky-ends. Any means, however, of cleaving the immobilised nucleic acid would suffice for this invention. Site specific chemical cleavage has been reported in Chu, B. C .F. and Orgel, L. E., Proc. Natl. Acad. Sci. U.S.A., 1985, 963–967. Use of a non-specific nuclease to generate blunt ended fragments might also be used. Preferably, though, a type II restriction endonuclease would be used, chosen for accuracy of recognition of its site, maximal processivity and cheap and ready availability.

The first or second sub-fragments may be sorted in step (b) by any sorting method suitable to generate sub-populations according to their sticky-end sequence. One method comprises dividing the sub-fragments into an array of samples, each sample in a separate. container; contacting the array of samples with an array of solid phase affinity matrices, each solid phase affinity matrix bearing a unique base sequence of same predetermined length as the first sticky end, so that each sample is contacted with one of the possible base sequences and the array of samples is contacted with all possible base sequences of that predetermined length for hybridisation to occur only between each unique base sequence and first sticky end complementary with one another; and washing unhybridised material from the containers.

Thus, a heterogeneous population of nucleic acids derived by cleavage with the sampling endonuclease, like fok1, can be sorted into sub-populations by 'pulling out' subsets of nucleic acids characterised by a particular sequence at the sticky-ends. One can isolate the sub-populations using, for example, beads coated with an oligonucleotide carrying a sticky-end complementary to that on the target subset of nucleic acids. The beads can then be isolated, washed and released into a clean container, which for the purposes of this process would preferably be a well in an array. Clearly any means of isolating cDNAs is usable in this invention, which includes immobilising complementary oligonucleotides onto any insoluble,-solid phase support. This might for example include affinity chromatography, inert beads and centrifugation or any similar means, but beads, magnetic or not, are preferred. Any appropriate container could be used but an array of wells would be preferred for use with liquid handling robots in an automated embodiment of the process.

In an alternative embodiment, cDNA fragments generated by the first cleavage with a type IIs restriction endonuclease to generate ambiguous sticky-ends can be sorted into sub-populations according to their sticky-ends using a hybridisation array. Typically, this method comprises (i) binding the sub-fragments to a hybridisation array comprising an array of oligonucleotide sets, each set bearing a unique base sequence of same predetermined length as the first sticky end and identifiable by location in the array, all possible base sequences of that predetermined length being present in the array, so that each sub-population bearing its unique first sticky end is hybridised at an identifiable location in the array; and (ii) determining the location to identify the first sticky end sequence.

For a 4 bp ambiguous sticky-end, every possible combination of bases can be accounted for with an array of 256 oligonucleotide sets.

Ideally, the fragments to be used would be the fragments free in solution generated by the first sampling endonuclease cleavage. These fragments would carry an adaptor at the 5' terminus. To allow for a second cleavage with a sampling endonuclease, the oligonucleotides on the array would have to carry a recognition site for the second sampling endonuclease.

The step of determining each second sticky-end sequence may be accomplished in a number of ways. By the use of the second sampling endonuclease, two further sub-fragments are generated.

Generally, immobilized fragments and fragments free in solution will have been generated. Either sets of fragments, both bearing ambiguous sticky-ends, could be analysed to determine additional sequence information.

Where a hybridisation array has been used to sort sub-fragments, the sub-fragments cut in step (c) are preferably those bound to the hybridisation array so that the further sub-fragments generated thereby remain bound to the hybridisation array. In this embodiment, the step (d) of determining each second stickyend sequence comprises contacting the further sub-fragments under hybridisation conditions with an array of adaptor oligonucleotides, each adaptor oligonucleotide bearing a label and a unique base sequence of same predetermined length as the second sticky end, the array containing all possible base sequences of that predetermined length, removing any unhybridised adaptor oligonucleotide, and determining the location of any hybridised adaptor oligonucleotide by detection of the label.

This embodiment is particularly advantageous because such arrays of oligonucleotides can be constructed in very small chips. of perhaps 2 mm$^2$ or less. This enables minimal quantities of reagents to be used and so high concentrations can be used to increase the hybridisation rate of adaptors, which is the rate limiting step of this process.

As an alternative, where sub-populations of sub-fragments have been sorted, the step of determining each second sticky-end sequence comprises isolating the further sub-fragments from step (c) and contacting the further sub-fragments with an array of adaptor oligonucleotides in a cycle, each adaptor oligonucleotide bearing a label and a unique base sequence of same predetermined length as the second sticky end, the array containing all possible base sequences of that predetermined length; wherein the cycle comprises sequentially contacting each adaptor oligonucleotide of the array with each sub-population of isolated sub-fragments under hybridisation conditions, removing any unhybridised adaptor oligonucleotide and determining the presence of any hybridised adaptor oligonucleotide by detection of the label, then repeating the cycle, until all of the adaptors in the array have been tested.

This particular part of the process may be termed "the adaptor cycle".

This part of the process is essentially sequencing by hybridisation and can be understood first by explaining it for the case of a single nucleic acid. Consider a single nucleic acid, immobilised at one terminus to a fixed insoluble matrix, that has been cleaved at the free terminus, as above, with fok1 thus generating a 4 bp ambiguous sticky-end.

To determine the sequence of that sticky-end one can probe the immobilised nucleic acid with an adaptor molecule. This would be an oligonucleotide carrying a sticky-end with one, known, sequence of 4 bp of the possible 256. The adaptor would additionally carry a fluorescent probe (and possibly a binding site for the sampling endonuclease). If the adaptor is complementary to the ambiguous end of the target nucleic acid, it will hybridise and it will then be possible to ligate the adaptor to the target. The immobilised matrix can then be washed to remove any unbound adaptor. To determine whether the adaptor has hybridised to the immobilised target, one need only measure the fluorescence of the matrix. This will alsb reveal how much of the adaptor has hybridised, hence the amount of immobilised cDNA. Other means of detecting hybridisation may be used in this invention. Radio-labeled adaptors could be used as an alternative to a fluorescent probe, so also could dyes, stable isotopes, tagging oligonucleotides, enzymes, carbohydrates, biotin amongst others.

The construction of adaptor oligonucleotides is well known and details and reviews are available in numerous texts, including: Gait, M. J. editor, 'Oligonucleotide Synthesis: A Practical Approach', IRL Press, Oxford, 1990; Eckstein, editor, 'Oligonucleotides and Analogues: A Practical Approach', IRL Press, Oxford, 1991; Kricka, editor, 'Nonisotropic DNA Probe Techniques', Academic Press, San Diego, 1992; Haugland, 'Handbook of Fluorescent Probes and Research Chemicals', Molecular Probes, Inc., Eugene, 1992; Keller and Manack, 'DNA Probes, 2nd Edition', Stockton Press, New York, 1993; and Kessler, editor, 'Nonradioactive Labeling and Detection of Biomolecules', Springer-Verlag, Berlin, 1992.

Conditions for using such adaptors are also well known. Details on the effects of hybridisation conditions for nucleic acid probes are available, for example, in any one of the following texts: Wetmur, Critical Reviews in Biochemistry and Molecular Biology, 26, 227–259, 1991; Sambrook et al, 'Molecular Cloning: A Laboratory Manual, 2nd Edition', Cold Spring Harbour Laboratory, New York, 1989; and Hames, B. D., Higgins, S. J., 'Nucleic Acid Hybridisation: A Practical Approach', IRL Press, Oxford, 1988.

Likewise, ligation of adaptors is well known and chemical methods of ligation are discussed, for example, in Ferris et al, Nucleosides and Nucleotides 8, 407–414, 1989; and Shabarova et al, Nucleic Acids Research 19, 4247–4251, 1991.

Preferably, enzymatic ligation would be used and preferred ligases are T4 DNA ligase, T7 DNA ligase, E. coli DNA ligase, Taq ligase, Pfu ligase, and Tth ligase. Details of such ligases are found, for example, in: Lehman, Science 186, 790–797, 1974; and Engler et al, 'DNA Ligases', pg 3–30 in Boyer, editor, 'The Enzymes, Vol 15B', Academic Press, New York, 1982. Protocols for the use of such ligases can be found in: Sambrook et al, cited above; Barany, PCR Methods and Applications, 1: 5–16, 1991; and Marsh et al, Strategies 5, 73–76, 1992.

If the adaptor is not complementary to the ambiguous sticky-end of the target nucleic acid then a second probe can be tried and the above process repeated until all 256 possible probes have been tested.

Clearly one of these will have to be complementary to the ambiguous end. Once this has been found, then the terminus of the target nucleic acid will carry also a binding site for the sampling endonuclease that will allow cleavage of the target nucleic acid exposing further bases for analysis and the above process can be repeated for the next 4 bp of the target. This iterative process can be repeated until the entire target nucleic acid has been sequenced.

In a further aspect, the present invention provides a method for identifying cDNA in a sample. The method comprises characterising cDNA as described above so as to obtain the sequences and relative positions of the reference site and first and second sticky-ends and comparing those sequences and relative positions with the sequences and relative positions of the reference site and first and second sticky-ends of known cDNAs, such as those available from DNA databases, in order to identify the or each cDNA in the sample. This method can be used to identify a single cDNA or a population of cDNAs.

In a further aspect, the present invention provides a method for assaying for one or more specific cDNAs in a sample. This assay method comprises performing a method of characterising CDNA as described above, wherein the reference site is predetermined, each first sticky-end sequence in sorting step (b) is a predetermined first sticky-end sequence and each second sticky-end sequence in step (d) is determined by assay of a predetermined second sticky-end sequence. In this assay method, the relative positions of the reference site and predetermined first and second sticky-ends characterise the or each specific cDNA. The assay method can be used to detect the presence of a single specific cDNA or a population of specific cDNAs. The reference site and first and second sticky-end sequences are preferably predetermined by selecting corresponding sequences from one or more known target cDNAs, such as those available from a DNA database.

The invention will now be described in further detail by way of example only, with reference to the following Example and the accompanying drawings V:

BRIEF DESCRIPTION OF THE FIGURES

FIG. 3 shows the structure of a preferred adaptor oligonucleotide;

FIG. 4 shows the structure of a self-removing adaptor oligonucleotide;

FIG. 5 shows a set of multiple dyes on oligonucleotide adaptors;

Figure 1:
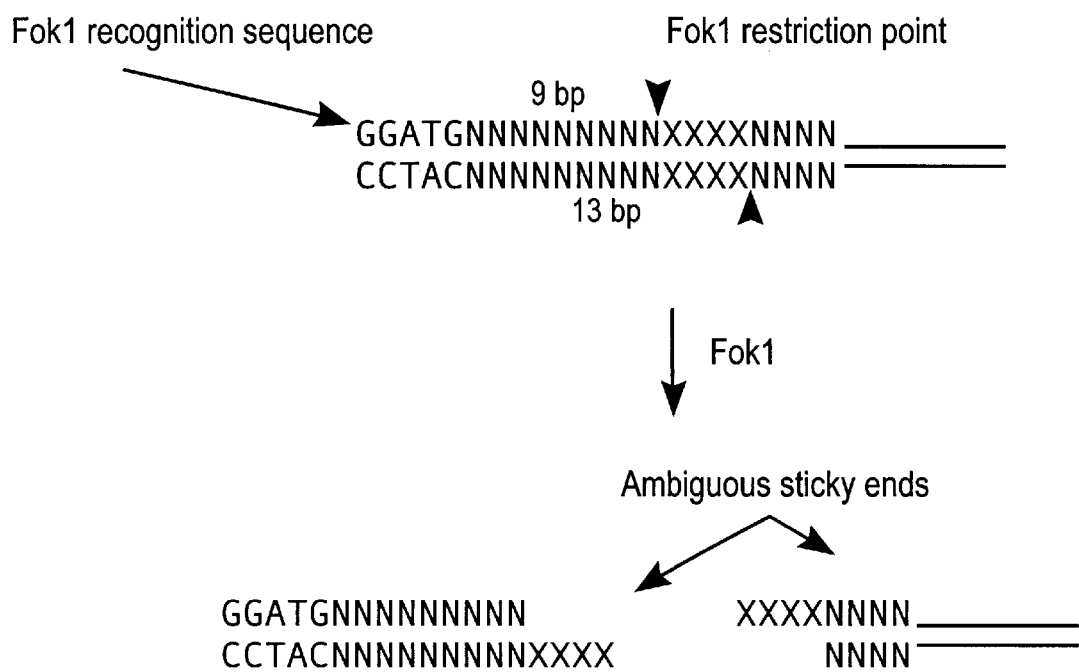
FIG. 1 shows the restriction behaviour of fok1.

The process of the invention can be applied to a heterogeneous population of immobilised nucleic acids allowing them to be analysed in parallel. To be successful when applied to a population of nucleic acids, this method relies on the fact that statistically 1 out of 256 molecules within the total population will carry each of the possible 4 bp sticky-ends after cleavage with fok1. The average human cell is estimated to express about 15000 distinct types of mRNA. If a cDNA population is sorted into 256 sub-populations by the sorting procedure described above, each will contain on average 60 different cDNAs given an mRNA population of about 15,000 transcripts. If these are then cleaved with fok1, one would expect that almost all will have different ambiguous sticky-ends (there is about a 1 in 1000 chance of there being 2 distinct cDNAs having the same initial 4 bp sticky end) so for most purposes one can assume that a hybridisation signal corresponds to a single cDNA type. Thus sequential addition of fluorescently labeled adaptors will allow the terminal 4 bp of a mixed population of cDNAs to be determined, resulting in 8 bp of signature in total for each cDNA in the population.

Fluorescence detectors can usually detect fluorescence of just a single molecule as long as the signal reaches the photomultiplier so choice in the design of immobilisation matrices is crucial to ensure the fidelity of the process. This means, however, that the hybridisation signal is quantitative, when using fluorescently labeled adaptors, which will reveal how many adaptor molecules have hybridised to the immobilised fragments. This is clearly directly proportional to the number of copies of each cDNA that is present. Thus each hybridisation signal will also reveal the relative proportion of each cDNA within the population. This can be related back to the in vivo levels of the mRNA by determining directly the quantity of a specific mRNA in vivo, preferably one with a high copy number like a housekeeping gene. The ratio of this quantity to the relative quantity of that mRNA as determined by the adaptor cycle will be the conversion factor to calculate the original in vivo quantities of each mRNA.

Detection of fluorescent signals can be performed using optical equipment that is readily available. Fluorescent labels usually have optimum frequencies for excitation and then fluoresce at specific wavelengths in returning from an excited state to a ground state. Excitation can be performed with lasers at specific frequencies and fluorescence detected using collections lenses, beam splitters and signal distribution optics. These direct fluorescent signals to photomultiplier systems which convert optical signals to electronic signals which can be interpreted using appropriate electronics systems. See, for example, pp 26–28 of PCT/US95/12678. A discussion of solid phase supports can also be found on pps 12–14 of that document.

Having acquired 4 bp of sequence information in the process of sorting cDNAs into subsets, one need only perform the adaptor cycle once to acquire an 8 bp signature for each CDNA in a well. Using a liquid handling robot, this can be performed simultaneously for all 256 wells generated by the sorting process.

Figure 2:
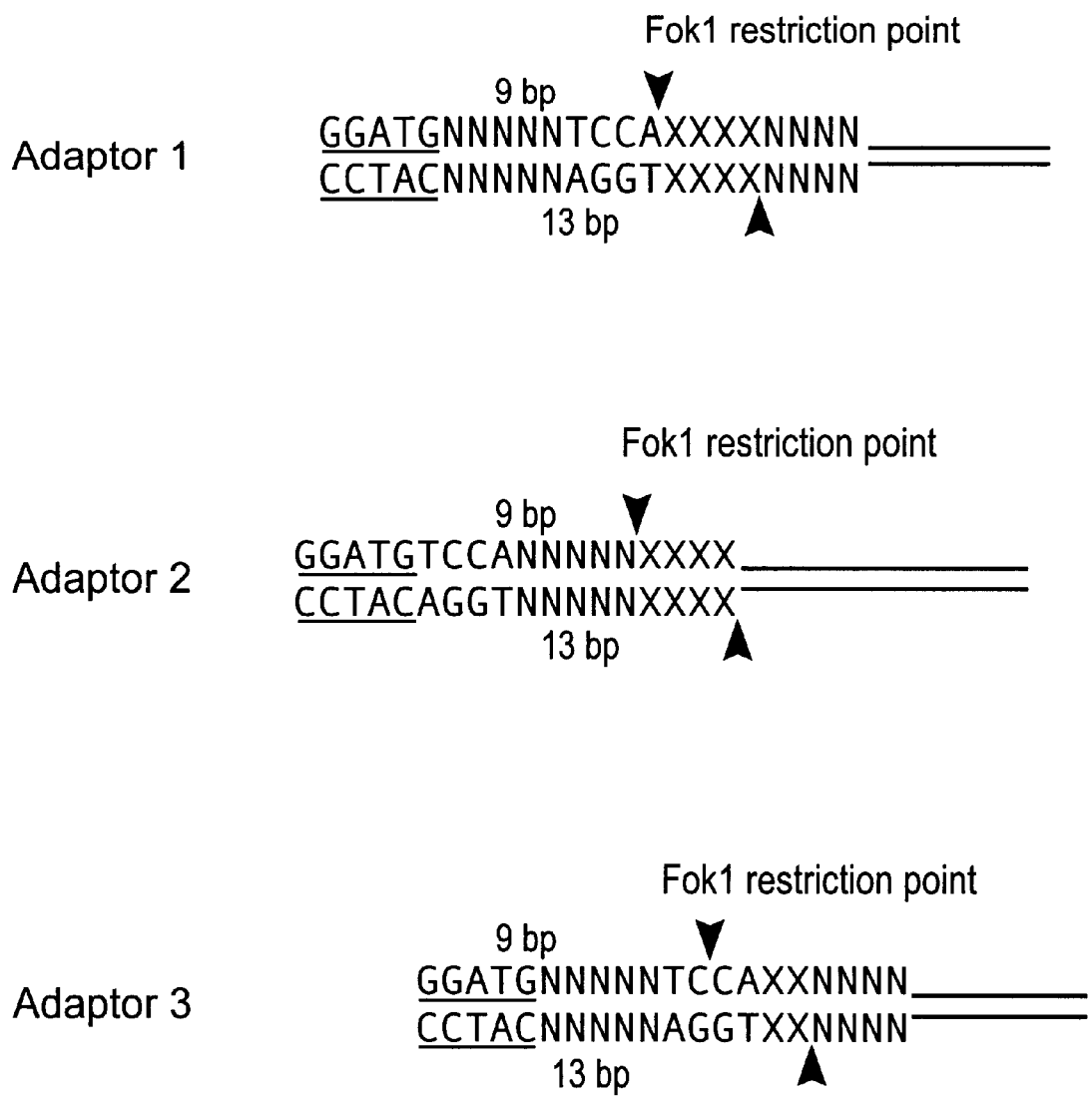
FIG. 2 shows the cutting behaviour of adaptor oligonucleotides.

The positioning of the recognition site for fok1 in the adaptor will determine whether the next 4 bp exposed are the next 4 bp in the sequence. Alternatively, they may overlap partially with the last four base pairs thus giving partially redundant information or they may be further downstream missing out a few bases, thus only sampling the sequence of the immobilised target nucleic acid. This is illustrated in FIG. 2. The cutting behaviour of adaptors with respect to which nucleotides are left single-stranded in the target nucleic acid is determined by the spacing between the fok1 recognition site and the target DNA. Sequential bases can be exposed with adaptor 1, while bases are sampled at intervals by adaptor 2. With adaptor 3, redundant information is acquired. Adaptor nucleic acid is shown and fok1 binding sites are underlined.

Whatever spacing is used, the spatial information relating the 4 bp oligonucleotides is retained. For the purposes of this invention a sampling approach is sufficient thus allowing the smallest and most economical adaptor to be constructed. FIG. 3 shows a preferred minimal adaptor for use in acquiring signatures in the present invention. The recognition sequence of fok1 is shown.

Figure 6A:
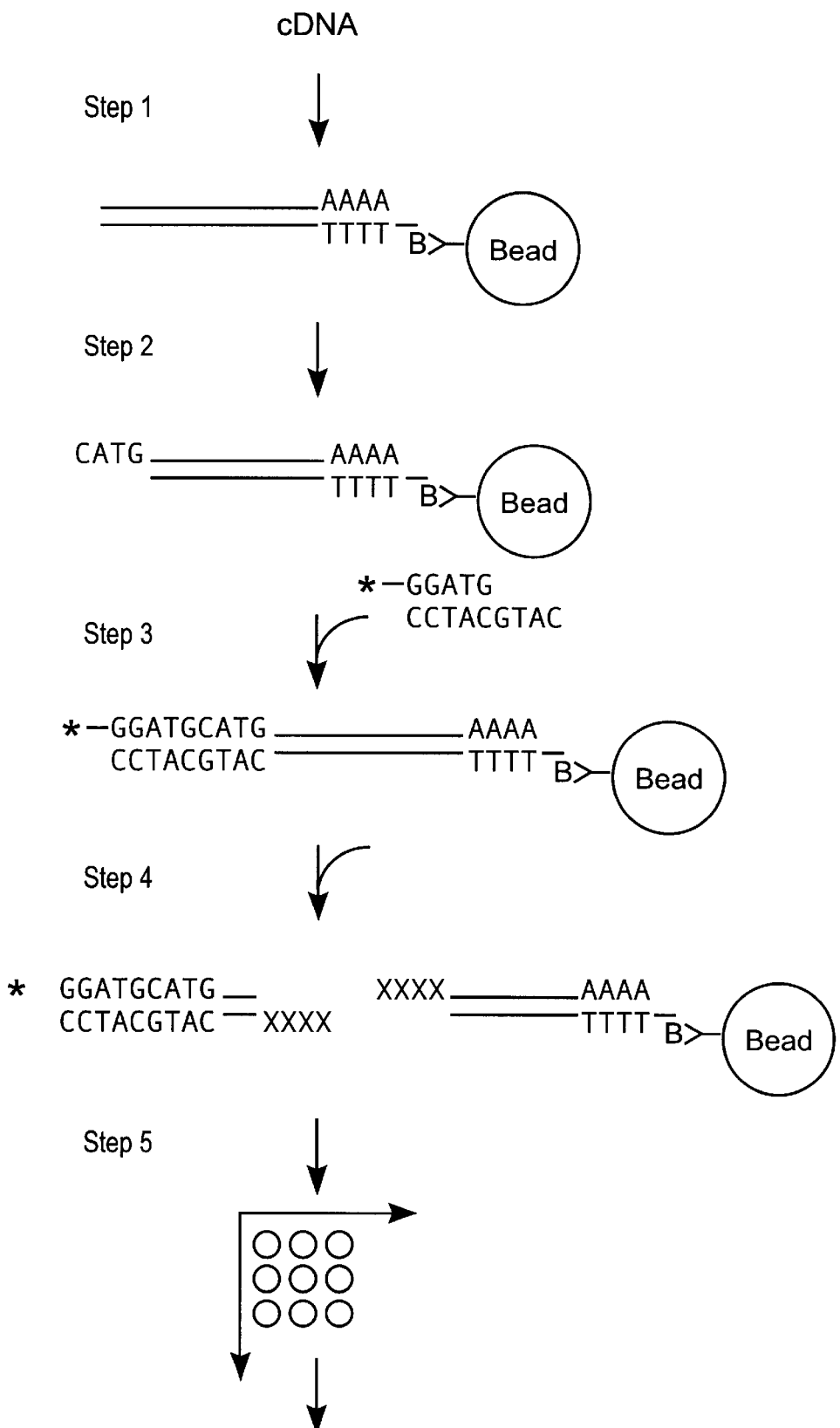
FIGS. 6a–c show a schematic representation of a process according to one embodiment of the invention.
Figure 6B:
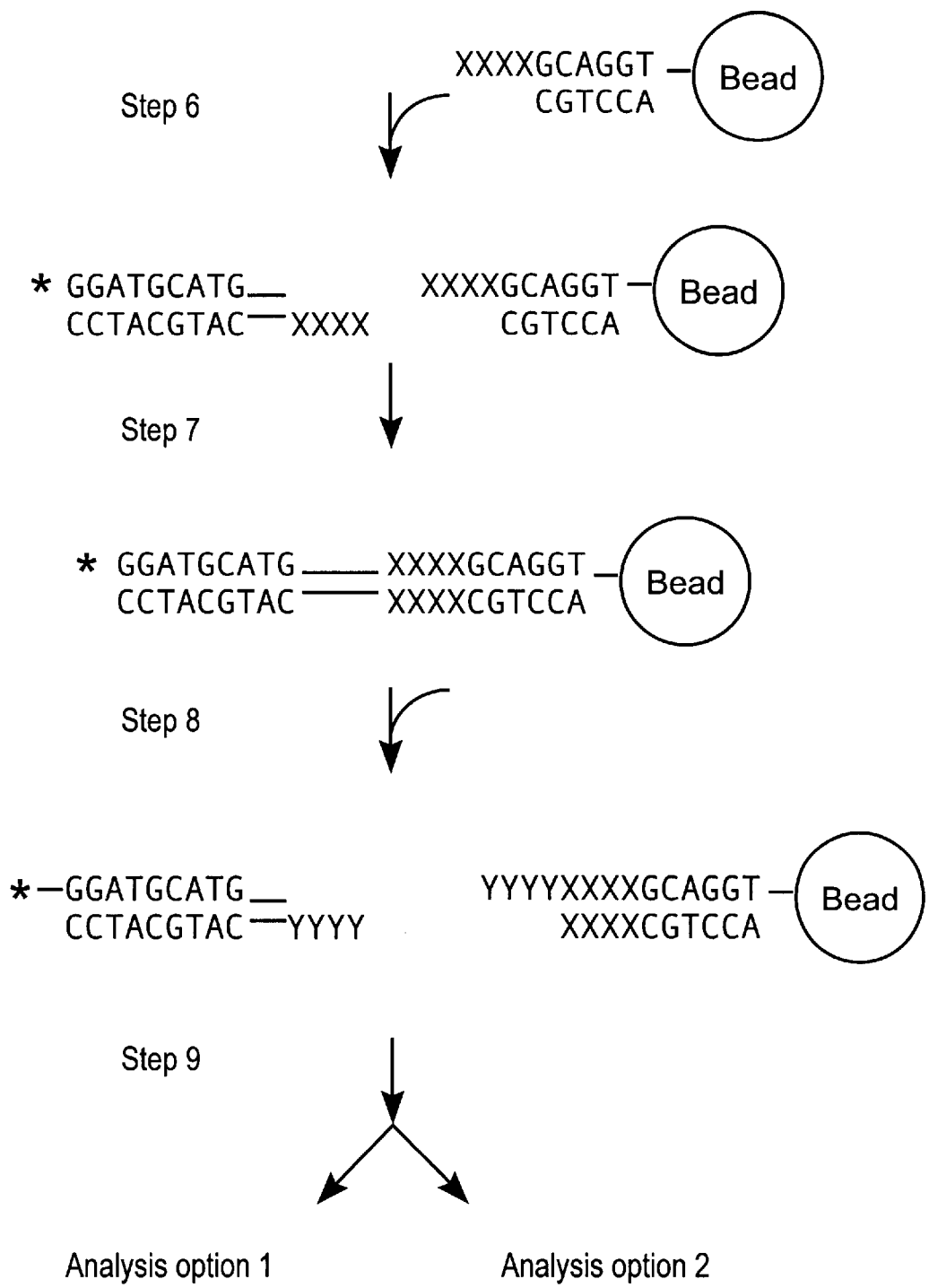
Figure 6C:
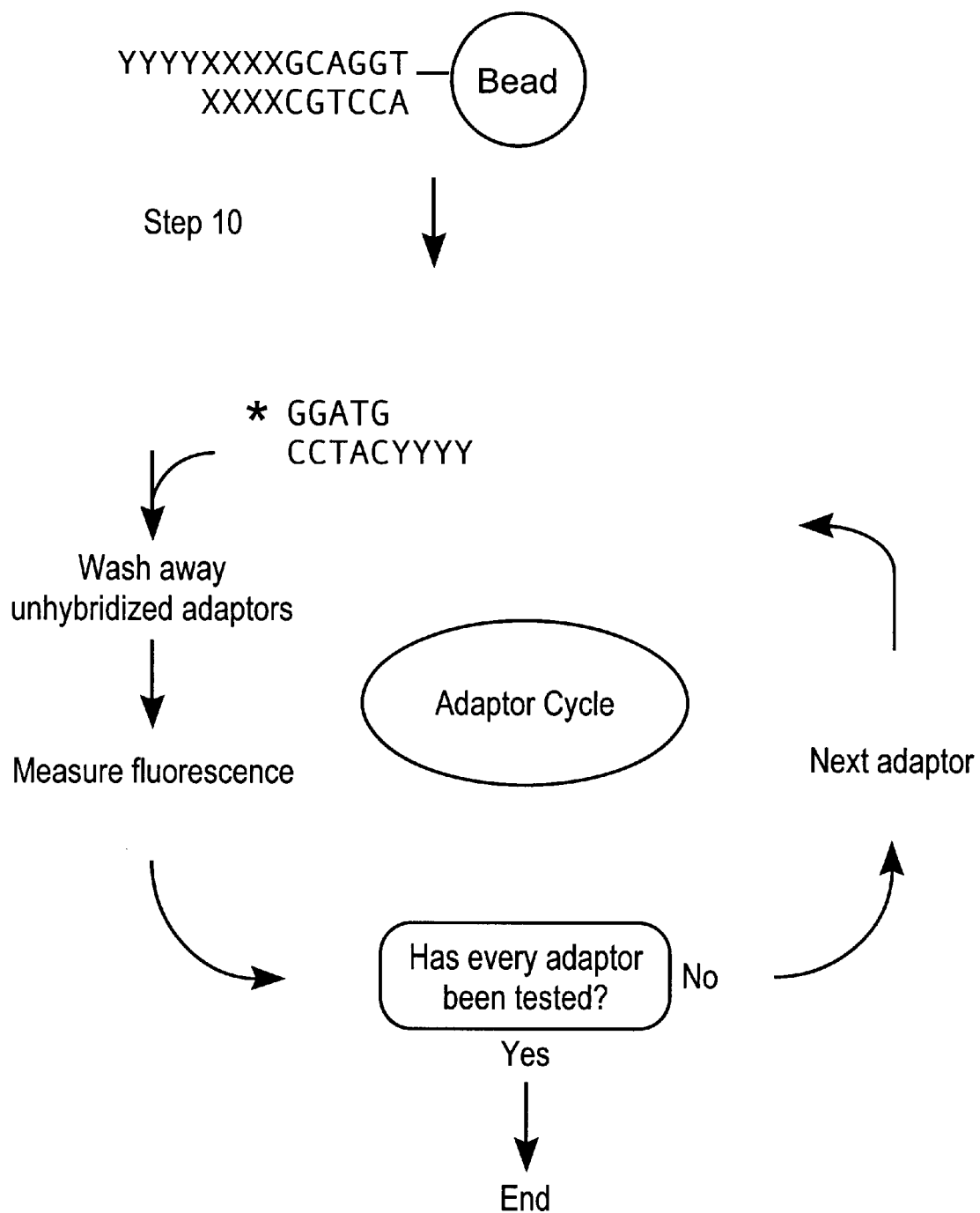

A preferred embodiment of the process is shown in FIGS. 6a to c. In step 1, mRNAs are immobilized by hybridisation to biotinylated poly-T. This allows capture of the population, after reverse transcription of the mRNA onto avidinated glass beads. In step 2, the poly-A carrying cDNAs are treated with the restriction endonuclease and loose fragments are washed away. In step 3, an adaptor oligonucleotide is added which bears a sticky-end complementary to the restriction endonuclease sticky-end. The adaptor carries a recognition site for the first sampling endonuclease and, optionally, a label. In step 4, the immobilized CDNA fragments are treated with the first sampling endonuclease so as to generate for the first time an immobilized fragment with a sticky-end and a fragment free in solution (steps 2 and 3 are only optional if the immobilized sticky-end fragment is to be analysed). In step 5 of this embodiment, the loose subfragments in solution are isolated from the immobilized subfragments and sub-divided into 256 wells. Each well contains an insoluble matrix, preferably beads, derivatised with oligonucleotides carrying sticky-ends complementary to one of the 256 possible sticky-ends. Thus, the beads in each well in step 6 will immobilize one of the 256 possible sticky-ends from the sample which are then ligated to the beads. Fragments that are not immobilized can then be washed way, thus generating a sorted population of 256 sub-populations of cDNA fragments.

In step 8, the second sampling endonuclease is added to each well containing the sub-population of immobilized fragments generated from step 7. The second sampling enzyme in this example is BspM1 whose recognition site is provided in the same sampling adaptor oligonucleotide attached to the bead.

The ambiguous sticky-end YYYY generated in step 8 is present on both the further sub-fragment in solution and the further subfragment immobilized to the bead. The further sub-fragments are therefore readily separable by washing the immobilized matrix to remove cleaved adaptors and reagent as shown in step 9.

At this stage in the process, one option for analysis is to enter the "adaptor cycle" with the immobilized fragments. This is discussed in further detail below. If the fragments to be analysed by the adaptor cycle are free in solution, then they must be immobilized first. As a second option, either fragment can be analysed further by a number of other methods. If the fragment is labelled with a fluorescent dye, one can determine the terminal sequence using a hybridisation chip. If the label is an immobilization effector, then cleavage fragments can be isolated, immobilized and analysed by a single base method.

Referring to step 10 in FIG. 6c, the further sub-fragment attached to the bead enters the adaptor cycle, as discussed in further detail below.

Figure 7A:
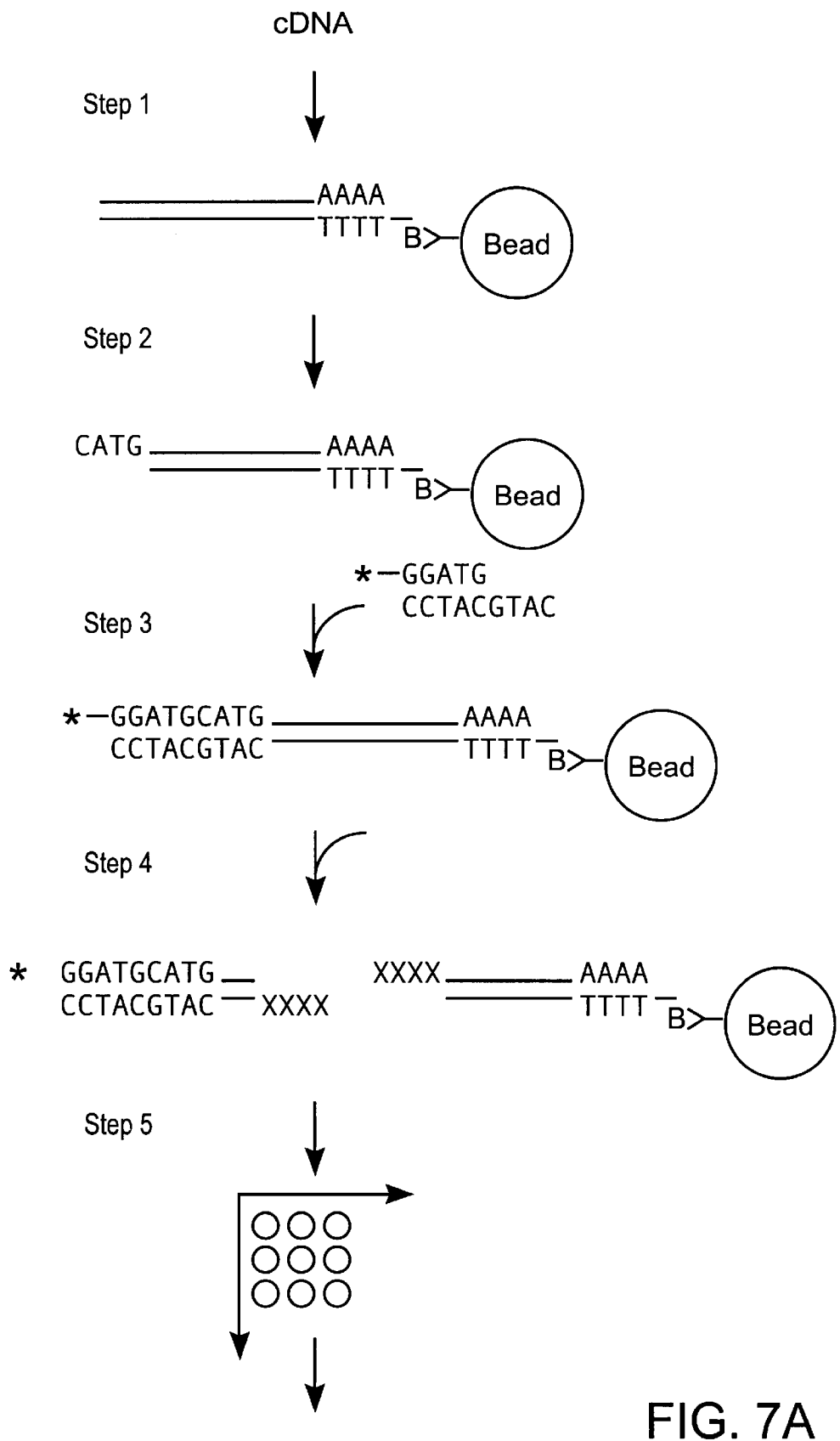
FIGS. 7a–c show a schematic representation of a process according to another embodiment of the invention.
Figure 7B:
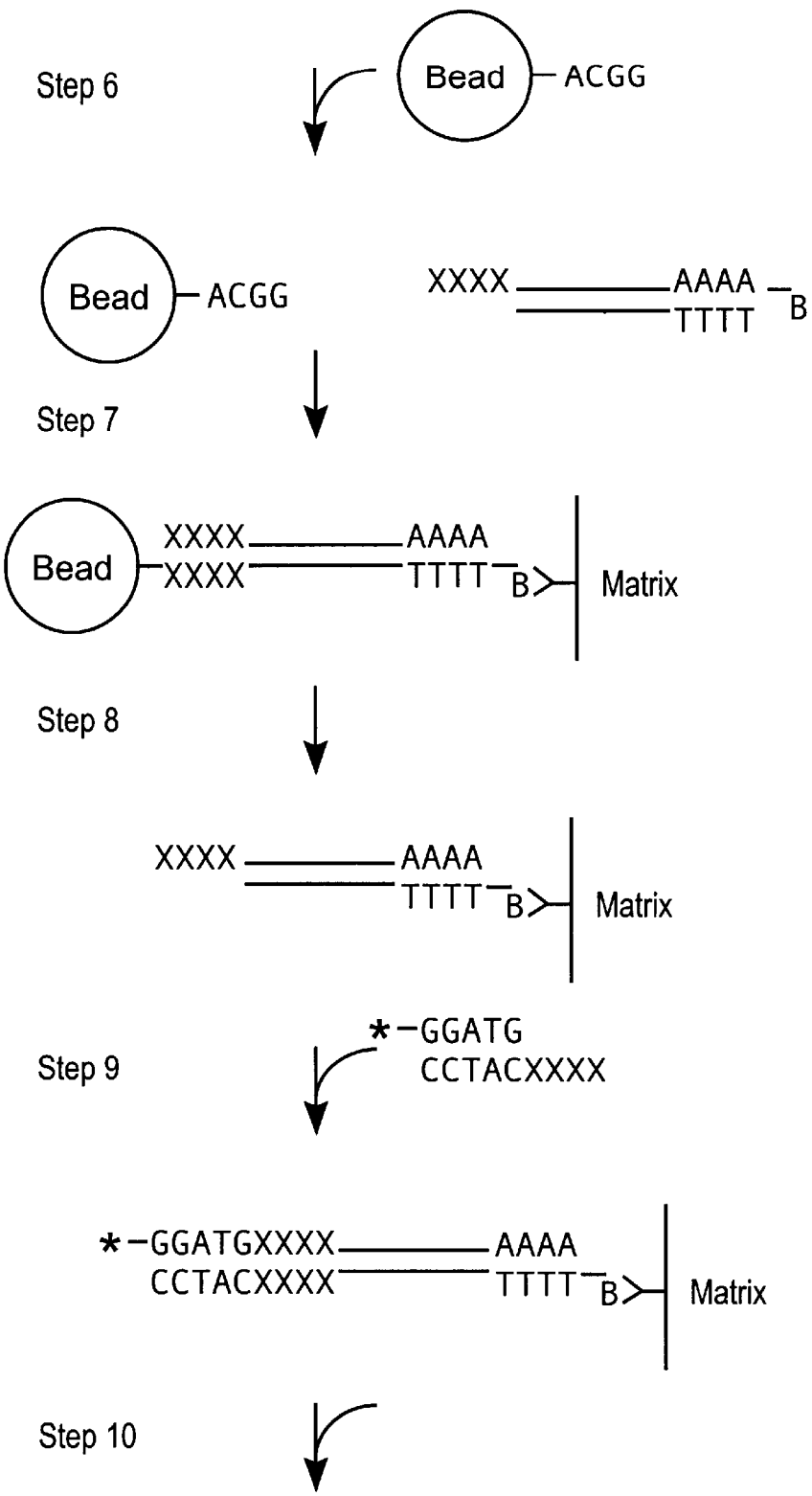
Figure 7C:
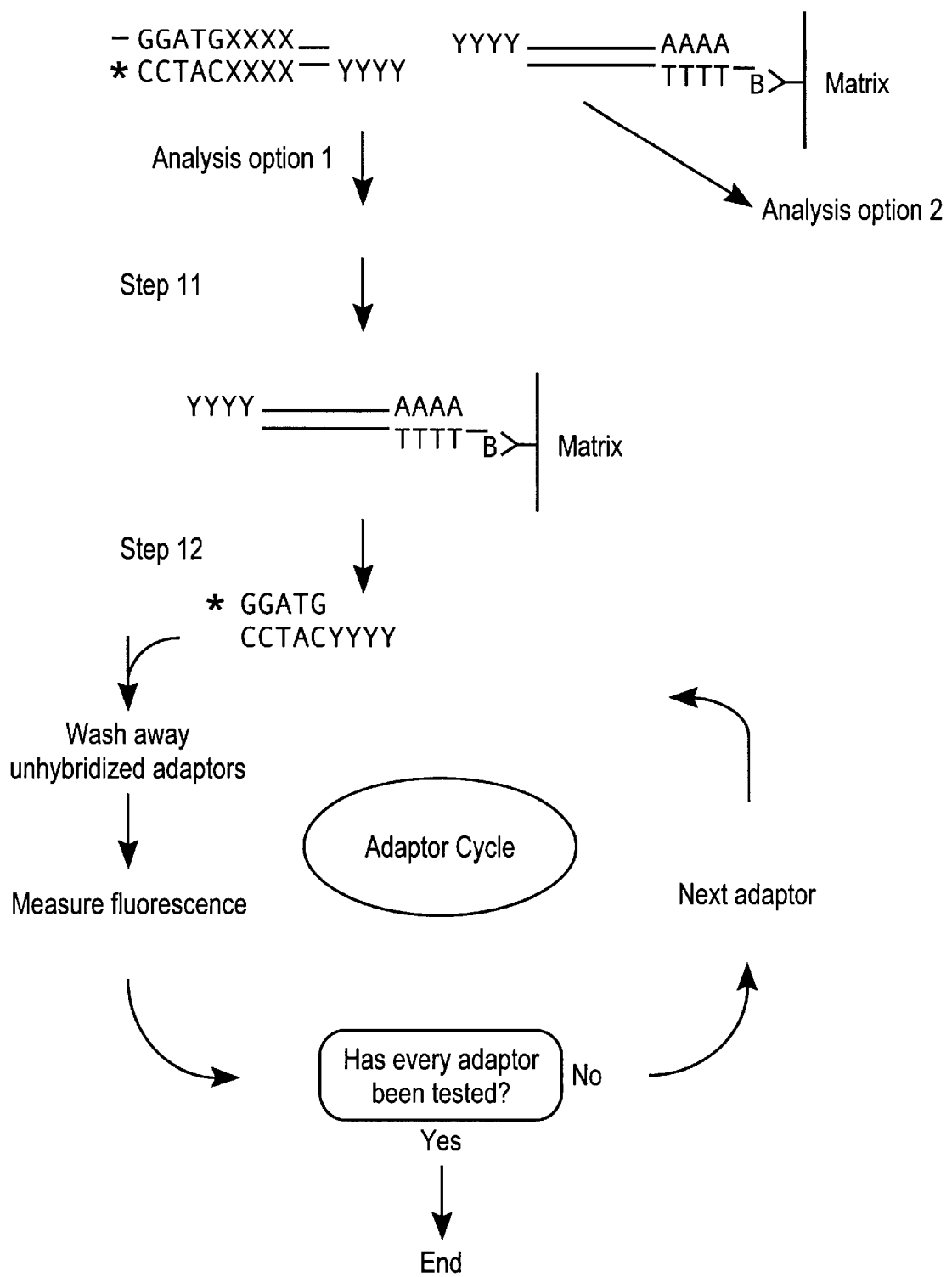
Figure 8:
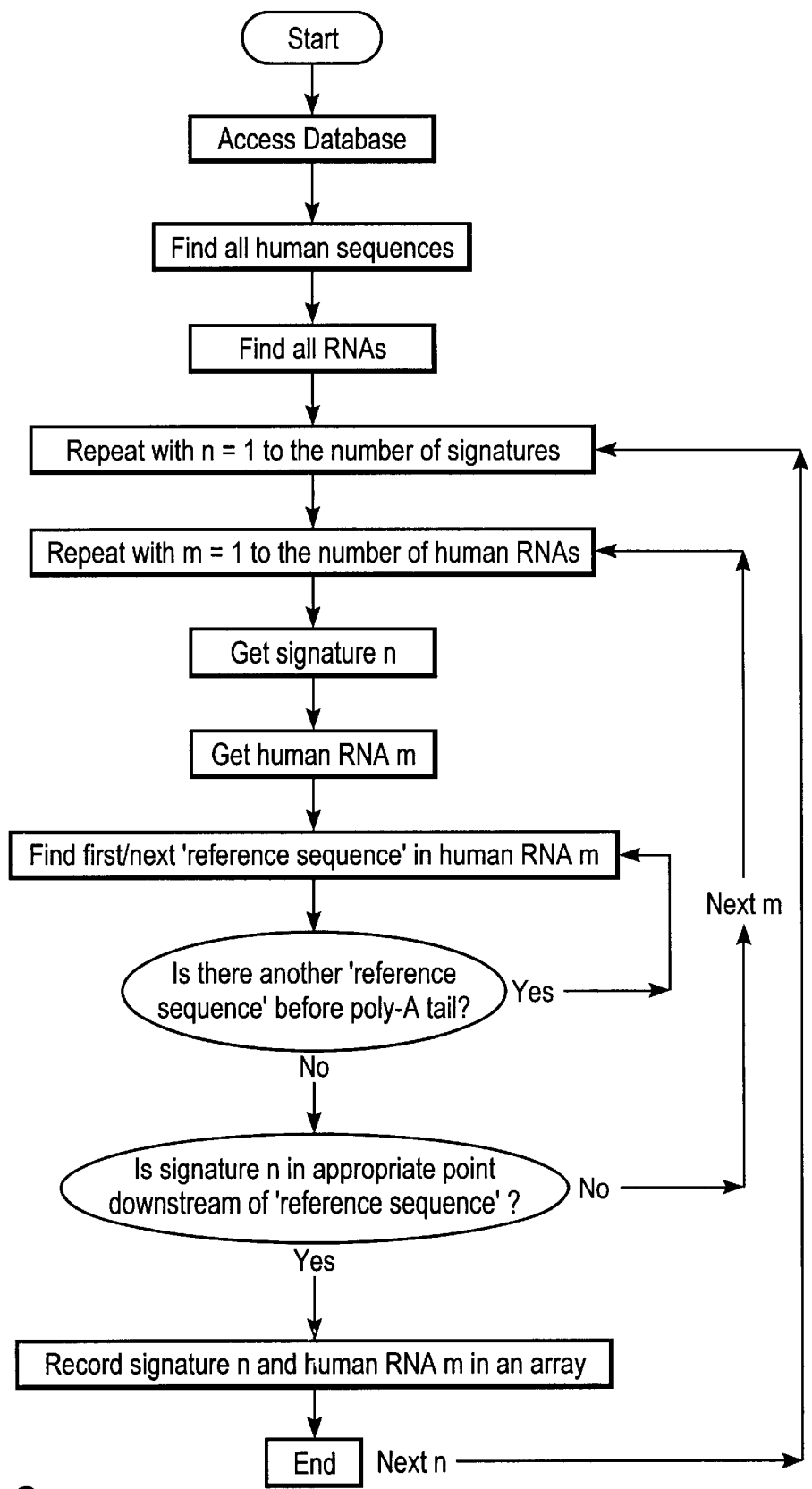
FIG. 8 shows an algorithm to search a sequence database to isolate human cDNAs corresponding to signatures.

In a second preferred embodiment of the invention as shown in FIGS. 7a to c, steps 1 to 4 are as described above. At step 5 it is the immobilized fragments that are sorted into sub-sets for further analysis. The cDNAs on beads are divided into 256 samples and the cDNAs from the beads are released and the beads recovered. At step 6 in FIG. 7b, to each well is added a magnetic bead bearing an oligonucleotide complementary to one of the possible 256 4 bp ambiguous sticky-ends generated by the first sampling endonuclease. After hybridisation, the beads are recovered and washed and each bead type binding a sub-population of the fragments bear a unique first sticky-end are released into one of 256 clean wells. The wells contain a matrix to immobilize cDNAs permanently, such as avidinated glass beads.

In step 8, the hybridisation conditions are altered to release the beads, which are then recovered. As a result of step 8, each well now contains beads with known first sticky-ends to which a known adaptor can be added carrying a recognition site for the same sampling endonuclease (in this case, fok1). Step 9 shows the step of adding the adaptor oligonucleotide, which is hybridised to the immobilized fragment. In step 10, the sampling endonuclease is added whereby a loose sub-fragment and an immobilized sub-fragment, each bearing the second sticky-end, are generated. Either of these fragments can be further analysed, as discussed in relation to the first embodiment.

Use of the adaptor cycle is further described in FIG. 6c for the first embodiment of the invention and in FIG. 7c for the second embodiment. Referring to FIG. 6c, the beads carrying the second sticky-end are analysed using the adaptor cycle at step 10. An adaptor oligonucleotide bearing a fluorescent label is added to the beads. The adaptor contains a unique sticky-end which will be complementary to one of the 256 possible four base second sticky-ends that might be present on the immobilized sub-fragment. The sequence of the sticky-end of each adaptor oligonucleotide is predetermined. Unhybridised adaptors are washed away and the fluorescence is measured. The cycle is repeated until all of the adaptors have been tested.

If a signature returns more than one sequence from a database, one can attempt to resolve these sequences by using the known signature information. If resolving sequences is required the adaptor cycle could be altered using adaptors of the form below shown in FIG. 4. This figure shows a self-removing adaptor in which the addition of a sampling endonuclease results in the adaptor cleavage of only the nucleotides it adds to the target nucleic acid, thereby re-exposing the bases whose sequence is being determined. The recognition sequence shown in the adaptor in the figure is that of BspM1.

After determining the- second quadrat of a signature using adaptors of the form above it would be possible to remove them and then if a particular signature had returned more than one sequence, a second adaptor specific to the terminal 4 bp could be added to acquire a further sample. Using an appropriate sampling enzyme this could be 2 or 3 or 4 further bp of sequence, depending on requirement but clearly fewer bases of additional sequence require fewer adaptors to determine the sequence of the resulting sticky-ends.

Once sequence information has been derived for a cDNA, perhaps by previous profiling, the present invention can be used to isolate a specific cDNA fragment using the same approach but focusing on one specific cDNA. Thus if the first 4 bp of signature are known then one can select for that subset of all cDNAs using the corresponding magnetic bead that would have been used in the sorting process. The sequence of the next 4 bp derived from the adaptor cycle could then be used to construct an adaptor carrying that appropriate sticky-end and a specific PCR primer. The desired cDNA could then be amplified using a general poly-T primer and the specific primer on the adaptor. The amplified fragment would provide a unique probe that could be used to identify the complete cDNA or mRNA on a Southern or Northern blot.

In order to speed up the adaptor cycle, adaptors can be added in groups so long as individual subsets of adaptors are each labeled with a different fluorescent marker to permit hybridisation of each adaptor subset to be distinguished. This sort of modification will still allow quantitative information to derived but 4 different photomultipliers would be required to detect each label. FIG. 5 shows the use of multiple dyes on adaptors which would allow groups of adaptors to be tested simultaneously.

One potential problem with the 'Adaptor Cycle' is to ensure that hybridisation of probes is accurate. There are major differences between the stability of short oligonucleotide duplexes containing all Watson-Crick base pairs. For example, duplexes comprising only adenine and thymine are unstable relative to duplexes of guanine and cytosine only. These differences in stability can present problems when trying to hybridise mixtures of short oligonucleotides ( e.g. 4 mers) to complementary target DNA. Low temperatures are needed to hybridise A-T rich sequences but at these temperatures G-C rich sequences will hybridise to sequences that are not fully complementary. This means that some mismatches may happen and specificity can be lost for the G-C rich sequences. At higher temperatures G-C rich sequences will hybridise specifically but A-T rich sequences will not hybridise.

In order to normalise these effects modifications can be made to the Watson-Crick bases. The following are examples but they are not limiting:

The adenine analogue 2,6-diaminopurine forms three hydrogen bonds to thymine rather than two and therefore forms more stable base pairs.

The thymine analogue 5-propynyl dU forms more stable base pairs with adenine.

The guanine analogue hypoxanthine forms two hydrogen bonds with cytosine rather than three and therefore forms less stable base pairs.

These and other possible modifications should make it possible to compress the temperature range at which random mixtures of short nucleotides can hybridise specifically to their complementary sequences.

It may also be possible to design smaller sets of adaptors with base analogs that bind to multiple bases such as deoxyinosine, 2-aminopurine or the like (Kong Thoo Lin et al, Nucleic Acids Research 20, 5149–5152). Such a set might have adaptors of the form below:

| GGATG     | GGATG     |
| CCTACAANG | CCTACANTG |

N would represent all 4 bases at that position. Thus each adaptor above represents a set of four adaptors. The two sets shown above would have only one common member. Each set would have one common member with four other sets. There are only 64 sets with N at the 3rd position in the sticky-end, similarly there are only 64 sets with N at the 2nd position. Hence to identify every base uniquely, 128 sets of adaptors could be used rather than the complete 256. To resolve the overlapping sets one might need to have some initial information about the number of cDNAs in each of the 256 samples. Sorted sets of cDNAs of the kind to be used in this process would have on average 60 cDNAs which could be resolved on a sequencing gel. If radiolabeled or fluorescently labeled the quantities of each cDNA could be determined. This might be valuable in order to save time as each adaptor set added in the adaptor cycle may take up to an hour to hybridise fully. Thus any means of increasing the speed of the process might be useful and worth the additional labour of producing the gels.

Clearly also a larger tissue sample might have to be used. Construction of redundant sets above would be made cheaper if bases with 'wobble' could be used to reduce degeneracy.

Various single base methods of analysing nucleic acids have been proposed and may be usable with the present invention. Most of these avoid gel techniques of DNA sequencing and potentially could be appropriate for analysing, in parallel, the subpopulations generated by the sorting process described above. Single base methodsare disclosed, for example, in U.S. Pat. No. 5,302,509; WO 91/66678; J. D. Harding and R. A. Keller, Trends in Biotechnology 10, 55–58, 1992; WO 93/21340; Canard et al, Gene 148, 1–6, 1994; Metzker et al, Nucleic Acids Research 22, 4259–4267, 1994; PCT/US95/03678; and PCT/GB95/00109.

Use a of hybridisation chips, grids or arrays would also be practical for use with this invention. An array of oligonucleotides would need to contain only 256 oligonucleotides corresponding to the 256 possible 4 bp sticky ends that would be generated by the second treatment of the cDNA fragments with the 'sampling enzyme'. If the fragments to be analysed are labeled with a fluorescent dye then the sticky-ends in each subset of cDNAs can be determined from the positions on the grid from which fluorescence is observed. Analysis using hybridisation grids will also provide quantitative information in the same way as the 'Adaptor Cycle'. Such methods are described in Lehrach et Poutska, Trends Genet. 2, 174–179, 1986; and Pevzner et al, Journal of Biomolecular Structure and Dynamics 9, 399–410, 1991.

As further information is acquired it will be possible to develop the process further for example to make use of database information.

Clearly with use of this process a significant database of signatures and their corresponding genes will be acquired. It is estimated that there may be as many as 10 000 housekeeping genes. For most purposes it is the tissue specific cDNAs that researchers will be interested in. The presence of the housekeeping genes will undoubtedly be expected and it will be extremely wasteful to have to identify these every time the process is used, except perhaps for calibrating expression levels. It will be possible using the adaptor cycle, to ignore certain subsets of cDNAs or miss out certain adaptors if the genes they identify are known housekeeping genes. This should greatly speed up the process of profiling a cell's cDNAs. Moreover it is highly likely that most adaptors will not hybridise to any sequences. If the tissue specific genes are already known, and information about abundance is all that is sought then only the adaptors corresponding to the expected signatures need be used.

These sorts of process modifications may require liquid-handling robotics that are flexible in their programming.

As a further modification, the choice of restriction endonucleases can be optimised. Since spatial correlation of bases and nucleotide frequencies are not random in the genomes of living organisms, it might be found empirically that certain combinations of sampling enzymes may resolve more sequences using the 8 bp signatures than. other combinations and clearly these would be of great value as it would save time spent on resolving signatures that return multiple sequences.

Similarly, once a database of cell-type specific genes is established, resolution steps will probably not be required as it will be known which genes, hence which signatures are to be expected in a given cell type.

Analysing cDNAs to determine sequence variation of alleleles of a particular gene is a further application that would be of great value to develop, in the context of analysing how these changes might alter patterns of gene expression in a cell. Variations in alleles may alter signatures and again these sorts of effects will only become apparent with use of this invention and will in the long term form another extremely useful database for improving the use of this invention.

EXAMPLE

Experimental Design

Three different PCR products were used to represent 3 different genes at varying expression levels. The PCR product used for this were exons 14,16 and 19 of the anion exchanger (AE1) as these PCRs have already been optimised in our laboratory. These will be referred to as AE14, AE16 and AE19.

The products were captured to Dynalbeads (by incorporating a biotin in one of the PCR primers) and effectively represent captured cDNA. AE16 was at half the concentration of AE14 and AE19 was at one fifth the concentration of AE14.

AE14 Sequence ccaaagctgggagagaacagaatgcct-
   tggttttctgctgcagatcttccaggaccacccactacagaagac
ttataactacaacgtgttgatggtgc-
   ccaaacctcagggcccctgcccaacacagccctcctctcccttgt
gctcatggccggtaccttcttctttgc-
   catgatgcgcaagttcaagaacagctcctatttccctggcaa
gtcagcatacctcctcgcctgtccttgccaacactgc AE16 Sequence ctgggagaatgccagggaaaggtctct-
   gcctcccaccctccaggcccagcccccaccctgtctctcacgtg
gtgatctgagactccaggaatatgag-
   gatgaagaccagcagagcaggcagggcggaggcaaaatcataaga
tgggaaactcggaacgcaagc-
   ccagtgggtggatgacccagcccgggctgaggagttgacaccttgaagcc
atcaggcaccgagagtttctgtgggaggggtagcaggtaagaatgccaagggc AE19 Sequence gtgataggcactgaccccagcctccgc-
   ctgcaggtgaagacctggcgcatgcacttattcacgggcatccag
atcatctgcctggcagtgctgtgggtg-
   gtgaagtccacgccggcctccctggccctgcccttcgtcctcatc
ctcactgtgccgctgcggcgcgtcct-
   gctgccgctcatcttcaggaacgtggagcttcagtgtgtgagtggc
tgcctgggcctggggcacaagagctgggagcatgcg Following capture, they were first digested with the frequent cutter Sau 3A1. This enzyme recognises the sequence GATC.

This provided the following 4 bp overhangs of each of the products.

AE14

```
            TTCCAGGACCACC...
      CTAGAAGGTCCTGGTGG...
```

AE16

```
            TGAGACTCCAGGAATAT...
```

-continued
```
            CTAGACTCTGAGGTCCTTATA...
```
AE19
```
            ATCTGCCTGGCAG...
      CTAGTAGACGGACCGTC...
```

The following adaptor complimentary to the 4 bp overhang revealed by Sau 3A1, and containing a Fok I site, was ligated to the captured fragments.

Adaptor SauFAM

```
   FAM - CTAGAGGACGATCGA.GGATG.
           GATCTCCTGCTAGCT.CCTAC.GATC
                                |
                             Fok I site
```

AE14

FAM-CTAGAGGACGATCGA.GGATG.GATC.TTCCAGGACCACC...
   GATCTCCTGCTAGCT.CCTAC.CTAG.AAGGTCCTGGTGG...

AE16

FAM-CTAGAGGACGATCGA.GGATG.GATC.TGAGACTCCAGGAATAT...
   GATCTCCTGCTAGCT.CCTAC.CTAG.ACTCTGAGGTCCTTATA...

AE19

FAM-CTAGAGGACGATCGA.GGATG.GATC.ATCTGCCTGGCAG...
   GATCTCCTGCTAGCT.CCTAC.CTAG.TAGACGGACCGTC...

These sequences were then digested with Fok I, which cuts at 9 and 13 bases from GGATG, and the following fragments were released into solution.

AE14

FAM - CTAGAGGACGATCGA.GGATG.GATC.TTCCA
         GATCTCCTGCTAGCT.CCTAC.CTAG.AAGGTCCTG

AE16

FAM - CTAGAGGACGATCGA.GGATG.GATC.TGAGA
         GATCTCCTGCTAGCT.CCTAC.CTAG.ACTCTGAGG

AE19

FAM - CTAGAGGACGATCGA.GGATG.GATC.ATCTG
         GATCTCCTGCTAGCT.CCTAC.CTAG.TAGACGGAC

The cleaved fragments were then captured, through ligation, to 3 different wells of a microtitreplate each containing a specific adaptor (which contains a site for BbvI 'GCAGC') simulating the first stage division into 256 subgroups and providing the first 4 bases. Bbv I cuts at 8 and 12 bases from GCAGC.

The full sequences are shown infra

For AE14 (adaptor Bbv14)

Biotin-N-GCAGC.AGA

```
                -continued

N-CGTCG.TCT.CAGG
                      |
                    Bbv I site

For AE16 (adaptor Bbv16)

Biotin-N-GCAGC.AGA

N-CGTCG.TCT.CCTC

For AE19 (adaptor Bbv19)

Biotin-N-GCAGC.AGA

N-CGTCG.TCT.GTCC
```

Where N is a number of bases
This produced the following sequences:

```
For AE14

Biotin-N-GCAGC.AGA.GTCCTGGAAGATC.CATCC.AGCTAGCAGGAGATC

N-CGTCG.TCT.CAGGACCTTCTAG.GTAGG.TCGATCGTCCTCTAG-FAM

For AR16

Biotin-N-GCAGC.AGA.GGAGTCTCAGATC.CATCC.AGCTAGCAGGAGATC

N-CGTCG.TCT.CCTCAGAGTCTAG.GTAGG.TCGATCGTCCTCTAG - FAM

For AE19

Biotin-N-GCAGC.AGA.CAGGCAGATGATC.CATCC.AGCTAGCAGGAGATC

N-CGTCG.TCT.GTCCGTCTACTAG.GTAGG.TCGATCGTCCTCTAG-FAM
```

At this point the concentration was measured through fluorescence of the FAM label and the first 4 bases (XXXX) determined.

Following this the fragments were digested with Bbv I and the next 4 bp revealed.

```
                For AE14

Biotin-N-GCAGC.AGA.GTCCT

N-CGTCG.TCT.CAGGACCTT

For AR16

Biotin-N-GCAGC.AGA.GGAGT

N-CGTCG.TCT.CCTCAGAGT

For AE19

Biotin-N-GCAGC.AGA.CAGGC

N-CGTCG.TCT.GTCCGTCTA
```

Following digestion 3 different adaptors, complementary to the 3 different 4 bp over hangs were then ligated to each well in turn to simulate the 'adaptor cycle' and the fluorescence measure at each stage.

These adaptors were

```
        AE14 (adaptor C14)
        GGAA.GATCCTGGACAGTTG
             CTAGGACCTGTCAAC-FAM AE16 (adaptor C16)
        CTCA.GATCCTGGACAGTTG
             CTAGGACCTGTCAAC-FAM AE19 (adaptor C19)
        AGAT.GATCCTGGACAGTTG
             CTAGGACCTGTCAAC-FAM
```

Successfully ligation, measured by fluorescence therefore provided concentration information and the next 4 bases (YYYY) of the 'tag'.

Tag—GATC.YYYY.N.XXXX

Where GATC corresponds to the Sau 3A1 site, XXXX the first 4 bases uncovered by the Fok I digestion which is separated by a single unknown base, N, to YYYY which corresponds to the next 4 bases revealed by Bbv I.

Materials and Methods

Adaptor Sequences and Preparation

SauFam

```
        5'-FAM-CTAGAGGACGATCGAGGATG-3'

3'-GATCTCCTGCTAGCTCCTACCTAG-PO4-5'
```

'Bbv" Adaptors

```
Bbv14
5'BIOTIN-6C-CCTAGACTAGAGGACCGATCGAATCAGCAGCAGA-3'

3'-GATCTGATCTCCTGGCTAGCTTAGTCGTCGTCTCAGG-PO4-5'

Bbv16
5'BIOTIN-6C-CCTAGACTAGAGGACCGATCGAATCAGCAGCAGA-3'
```

-continued

```
3'-GATCTGATCTCCTGGCTAGCTTAGTCGTCGTCTCCTC-PO4-5'
```

Bbv19
```
5'BIOTIN-6C-CCTAGACTAGAGGACCGATCGAATCAGCAGCAGA-3'

3'-GATCTGATCTCCTGGCTAGCTTAGTCGTCGTCTGTCC-PO4-5'
```

Cycling Adptors

C14
```
5'FAM-CAACTGTCCAGGATC-3'

3'-GTTGACAGGTCCTAGAAGG-PO4-5'
```

C16
```
5'FAM-CAACTGTCCAGGATC-3'

3'-GTTGACAGGTCCTAGACTC-PO4-5'
```

C19
```
5'FAM-CAACTGTCCAGGATC-3'

3'-GTTGACAGGTCCTAGTAGA-PO4-5'
```

BioFAMFok

```
5'BIOTIN-GGTCACTTAGATCGATCCATGAGGATGCTTCATTCTGATTCAGTCC-3'

3'-CCAGTGAATCTAGCTAGGTACTCCTACGAAGTAAGACTAAGTCAGG-FAM
```

BioG

```
5'BIOTIN-GCATCTGGAGTCTACAGTCGTCTATTGACG-3'

3'-CGTAGACCTCAGATGTCAGCAGATAACTGCCGGC-PO4-5'
```

GCCG

```
    5'FAM-GCATCAGGATGTACAG-3'

3'-CGTAGTCCTACATGTCGCCA-PO4-5'
```

FAM- fluorescein    PO4 - phosphate

All primers were purchased from Oswell DNA Services.

All adaptors were made but heating 200 ul of TE containing each primer at 20 pmol/ul concentration at 90° C., in a Techne Dryblock and allowing the block to cool to room temperature over 2 hours. The adaptors were then incubated on ice for 1 hour and then frozen at −20° C. until used.

Binding Bbv14,16, and 19 Adaptors to Microtitre Plate

In order to capture the Fok 1 cleaved fragments to the 'Bbv' adaptors via ligation the 'Bbv" adaptors were bound to black, streptavidin coated 96 well microtitre plates (Boehringer Mannheim). This was achieved by incubating 10 pmol of the appropriate adaptor in 35 ul of 1×TE+0.1M NaCl in each well overnight at 4° C. Following the overnight incubation each well was washed 3 times with 50 ul of 1×TE+0.1M NaCl. The 1×TE+0.1M NaCl was removed and 50 ul of 1×ligase buffer was added to each well and the plate was stored at 4° C. until used.

Plate Capacity

To determine the binding capacity of each well 10 pmol of BioFAMFok adaptor was bound to 8 wells by incubating lopmol of the adaptor in 25 ul of 1×TE+0.1M NaCl in each well overnight at 4° C. Following the overnight incubation each well was washed 3 times with 50 ul of 1×TE+0.1M NaCl. A dilution of BioFAMFok (5, 2.5, 1.25, 0.675, 0.3375 pmol) diluted in 1×TE+0.1M NaCl was added. to a series of well and the fluorescence of the plate read in a Biolumin Microtiter plate Reader (Molecular Dynamics).

The following readings (expressed as Relative Fluorescent Units) was obtained.

Dilution Wells

| | |
|---|---|
| 5 pmol | 74575 RFU |
| 2.5 pmol | 35429 RFU |
| 1.25 pmol | 16232 RFU |
| 0.625 pmol | 9388 RFU |
| 0.3375 pmol | 4807 RFU |

Wells incubated with lopmol of adaptor and washed

20872 RFU
21516 RFU
22519 RFU
21679 RFU
22658 RFU
21517 RFU
21742 RFU
22417 RFU
mean 21865

From these figures one can calculate that 21856 RFUs is equal to 1.5 pmol of BioFAMFok. This data agree with the capacity of the wells to bind biotinylated double stranded DNA (5 pmol hybridised in 200 ul) provided by Boehringer Mannheim technical help line.

Effect of Tween20 on Ligation

The addition of 0.1% Tween 20 to the reaction buffer used with Fok 1 is claimed to reduce the exonuclease activity associated with this enzyme (Fok 1 data sheet—New England Biolabs). The following experiment was performed in order to determine if the addition of Tween would have any effect on the subsequent ligation of the cleaved fragments.

Nine reactions were set up with each set of three reactions each containing either 0, 0.05 or 0.1% tween in 25 ul of 1×ligase buffer, 10 pmol BioG adaptor, 10 pmol GCCG adaptor and 200 ul ligase (New England Biolabs) . One set of three reactions was set up as the above with 0.1% tween and no ligase. These were then incubated at 16° C. for 1 hours and then each reaction transferred to a well of a black streptavidin coated microtitre plate (Boehringer Mannheim). The plate was incubated at room temperature for one hour and each well washed 3 times with 100 ul of TES and the fluorescence measured in a Biolumin Microtiter plate Reader (Molecular Dynamics).

The following readings (expressed as Relative Fluorescent Units) was obtained.

| 0% tween 20 | 0.05% tween 20 | 0.1% tween 20 | 0.1% tween 20 (no ligase) |
|---|---|---|---|
| 8592 | 8742 | 10213 | 3660 |
| 8083 | 8712 | 10605 | 3967 |
| 8720 | 8519 | 11598 | 3468 |
| 8465 | 8657 | 10805 | 3698-means |

The above data demonstrate that the inclusion of 0.1% tween 20 increases ligation efficiency and therefore should not be detrimental to the ligation of the Fok 1 cleaved fragments to the 'Bbv" adaptors.

PCR Primers and Conditions and Purification

The 3 PCR products used to represent cDNA transcripts at different concentrations were exons 14,16 and 19 from the human erythrocyte anion exchanger gene located on chromosome 17q21–22.

Primer sequences use to amplify exons 14,16 and 19

Exon 14
  Forward primer
    5'-GTATTTTCCAGCCCAAGCCAAAGCTGG-3'
  Reverse primer
    5'BIOTIN-GCAGTGTTGGCAAGGACAGGC-3'
Exon 16
  Forward primer
    5'BIOTIN-GCCCTTGGCATTCTTACCTGC-3'
  Reverse primer
    5'-CTGGGAGAATGCCAGGGAAAGG-3'
Exon 19
  Forward primer
    5'-GTGATAGGCACTGACCCCAG-3'
  Reverse primer
    5'BIOTIN-CGCATGCTCCCAGCTCTTGTGC-3'

The inclusion of biotin into one of the primers in each set will allow their capture to streptavidin coated beads (Dynal UK)

All PCR reactions were performed in 50 ul containing 1×Amplitaq buffer (Perkin Elmer), 30 pmol of forward and reverse primer, 200 uM dNTPs, 1.25 units of Amplitaq (Perkin Elmer) and 100 ng of human genomic DNA. The reactions were overlaid with 50 ul of mineral oil and cycled on a Techne 'Genie' PCR machine with the following conditions.

Exon 14
  1 cycle 95° C. for 2 min
  35 cycles 57.5° C. for 45 sec, 72° C. for 1 min, 95° C. for 35 sec
  1 cycle 72° C. for 5 min
Exon 16
  1 cycle 95° C. for 2 min
  35 cycles 52° C. for 45 sec, 72° C. for 1 min, 95° C. for 35 sec
  1 cycle 72° C. for 5 min
Exon 19
  1 cycle 95° C. for 2 min
  35 cycles 57.5° C. for 45 sec, 72° C. for 1 min, 95° C. for 35 sec
  1 cycle 72° C. for 5 min Purification Excess primers and salts need to be removed before the PCR products are bound to DynaBeads, this is performed as described below.

10 reactions of each were pooled following PCR, separately, prior to purification. The PCR products were then ethanol precipitated by adding 2.5 volumes of 100% ethanol and one tenth of a volume of 3M sodium acetate. The solution was then incubated at −20° C. for 30 minutes and then spun at 13000 rpm in a Heraeus A13 benchtop centrifuge for 15 minutes to precipitate the DNA. The supernatant was then poured off and the pellet allowed to air dry. The dry pellet was then resuspended in 150 ul of water. Following this, 2 Chromospin-100 columns (Clonetech) were prepared for each sample by spinning the columns in a Hereaus 17RS centrifuge for 3 minutes at 3500 rpm according to the manufacturer's instructions. Following centrifugation 75 ul of the DNA solution was added to each prepared column and spun as before collecting the purified DNA into a 1.5 ml eppendorf tube. The 2 samples for each exon were then pooled and the DNA concentration measured-by reading the absorption at 260 nm and 280 nm in a Pharmacia Genequant spectrophotometer.

Solutions and Buffers
  1×TE pH7.6
  10 mM Tris HCl
  1 mM EDTA
  TES pH7.5
  10 mM Tris-HCl
  1 mM EDTA
  2M NaCl
  1×Fok I buffer pH7.9
  50 mM potassium acetate
  20 mM Tris Acetate
  10 mM magnesium acetate
  1 mM DTT
  1×Bbv I buffer Ph7.9
  50 mM NaCl
  10 mM Tris-HCl
  10 mM MgCl2
  1 mM DTT
  1×Sau 3A buffer pH7.9
  33 mM Tris acetate
  66 mM potassium acetate
  10 mM magnesium acetate
  0.5 mM DTT
  1×Ligase buffer pH7.8
  50 mM Tris-HCl
  10 mM MgCl2
  10 mM DTT
  1 mM ATP
  50 ug/ml BSA Results Concentrations of Column Purified DNA
  exon 14—130 ng/ul
  exon 16—120 ng/ul
  exon 19—115 ng/ul
  1 ug exon14 (255 bp)=5.9 pmol, 1 ug exon16 (272 bp)=5.58 pmol, 1 ug exon19 (252 bp)=6.03 pmol
  1 ug exon14=7.7 ul, 1 ug exon16=8.3 ul, 1 ug exon19=8.7 ul therefore exon 14=0.76 pmol/ul, exon 16=0.67 pmol/ul, exon 19=0.69 pmol/ul Sau 3A1 Digest 30, 15 and 6 pmol of column purified exons 14, 16 and 19, respectively, were digested with 20 units of Sau 3A1 in 100 ul of 1×Sau 3A1 buffer at 37° C. for 4 hours.

| | |
|---|---|
| exon14 | 39.5 ul |
| exon16 | 22.4 ul |
| exon19 | 8.7 ul |
| Sau 3A1 | 5 ul |
| 10 × Sau 3A1 buffer | 10 ul |
| H2O | 14.4 ul |

Following digestion the reaction mix was heated at 65° C. in a Techne Dryblock for 20 minutes to inactivate the enzyme.

Preparation of DynaBead M280

According to the manufacture's instructions 3 mg of DynaBeads M280 will bind 60–120 pmol of biotinylated double stranded DNA.

300 ul of DynaBeads M280 at 1 mg/ml were washed with 100 ul TES by holding the beads to the side of an eppendorf tube with a Magnetic Particle Concentrator (Dynal UK) so that the supernatant could be removed. This was repeated three times (All subsequent bead manipulation were carried out in this manner according to manufacture's instructions). The beads were resuspended in 100 ul of TES and the Sau 3A1 digested DNA added and incubated at room temperature for 1 hour to allow the biotinylated DNA to bind to the beads.

The Beads/DNA were then washed three times with 1×ligase buffer using the Magnetic Particle Concentrator (Dynal UK) as before.

Ligation of SauFAM Adaptor (Containing Fok I Site)

The supernatant was removed and the beads/DNA were resuspended in 75 ul of 1×ligase buffer containing 300 pmol of SauFAM adaptor and 4000 units of ligase (New England Biolabs).

Beads/DNA, 7.5 ul 10 ligase buffer, 15 ul SauFAM (at 20 pmol/ul), 10 ul ligase (at 400 units/ul), 42.5 ul H2O.

The reaction was then incubated at 16° C. for 2 hours.

Fok I Digestion

Following ligation the beads/DNA were was 2 times with 75 ul of 1× Fok I buffer and the resuspended in 10 ul of 1×Fok I buffer and heated at 65° C. in a Techne Dryblock for 20 minutes to inactivate any remaining ligase. The buffer was was removed and the beads/DNA resuspended in 95 ul of 1× Fok I buffer containing 20 units of Fok I (New England Biolabs).

Beads/DNA, 9.5 ul 10×Fok I buffer, 5ul Fok I (at 4 units/ul)

The beads/DNA were then incubated at 37° C. for 2 hours.

Following incubation the supernatant, containing the fragments cleaved by Fok I, was then transferred to a fresh eppendorf tube and heated at 65° C. for 20 minutes in a Techne Dryblock in inactivate the Fok I.

Ligation of Fok I Cleaved Fragments to Bbv Adaptors on Microtiter Plate

The Fok I fragments were then divided into three tubes each containing 30 ul of Fok I cleaved fragments, 5 ul of 10×Ligase buffer, 3 ul ligase (at 400 uints/ul—New England Biolabs) and 12 ul of H2O.

The ligase buffer on a plate containing adaptors Bbv14, 16, 19 in separate wells (prepared as previously described) was removed and the above reaction mixtures, containing the Fok I cleaved fragments and ligase, added to each.

The wells were then incubated at 16° C. for one hour and then washed three times with 50 ul of TES. The TES was removed from the wells, another 50 ul of TES added and the fluorescence measured in Biolumin Microplate reader (Molecular Dynamics). A well to which no fragments were added and just contained Bbv adaptors was used as a blank.

Data Expressed as RFUs

| | |
|---|---|
| Bbv14 well | 1774 RFU |
| Bbv16 well | 1441 RFU |
| Bbv19 well | 1192 RFU |
| Blank | 1010 RFU |

The reading from the blank well, which is a background reading, was subtracted from the reading of the other wells and gave the following.

| | |
|---|---|
| Bbv14 well | 764 RFU |
| Bbv16 well | 431 RFU |
| Bbv19 well | 182 RFU |

As half as much of exon 16 compared to exon 14 (15 pmol exon 16, 30 pmol exon 14) was included into the procedure the reading obtained from the Bbv16 well should be half (i.e. 50%) of that obtained from the Bbv14 well and as one fifth the amount of exon 19 compared to exon 14 (6 pmol exon 19, 30 pmol exon 14) the reading obtained from the Bbv19 well should be one fifth (i.e. 20%) that obtained from the Bbv14 well.

Ideal Reading Expressed As Percentages

| | |
|---|---|
| Bbv14 well | 100 |
| Bbv16 well | 50 |
| Bbv19 well | 20 |

Actual Readings Expressed As Percentages (using Bbv14 well as 100%)

| | |
|---|---|
| Bbv14 well | 100 |
| Bbv16 well | 56.4 |
| Bbv19 well | 23.8 |
| Bbv16 well | 6.4% error |
| Bbv19 well | 3.8% error |

Therefore, this process is capable of separating a mixed population of DNA, and identifying 4 bp, while at the same time maintaining the relative proportions of the original mixture with minimal errors. Which in turn can then be reprobed to obtain another 4 bp and the associated quantitative data.

What is claimed is:

1. A method for characterizing CDNA, which comprises:
   (a) cutting a sample comprising a population of one or more cDNAs or isolated fragments thereof, each having a strand complementary to the 3' poly-A terminus of an mRNA and bearing a tail, with a first sampling endonuclease at a first sampling site of known displacement from a reference site proximal to the tail to generate from each cDNA or isolated fragment thereof a first and second sub-fragment, each comprising a sticky end sequence of predetermined length and unknown sequence, the first sub-fragment bearing the tail;
   (b) sorting either the first or second sub-fragments into sub-populations according to their sticky end sequence and recording the sticky end sequence of each sub-population as the first sticky end;
   (c) cutting the sub-fragments in each sub-population with a second sampling endonuclease, which is the same as or different from the first sampling endonuclease, at a second sampling site of known displacement from the first sampling site to generate from each sub-fragment a further sub-fragment comprising a second sticky end sequence of predetermined length and unknown sequence; and
   (d) determining each second sticky end sequence; wherein the aggregate length of the first and second sticky end sequences of each sub-fragment is from 6 to 10; and wherein the sequences and relative positions of the reference site and first and second sticky ends are utilized to characterize the cDNA or cPNAs.

2. A method according to claim 1, wherein the sample cut with the first sampling endonuclease comprises isolated fragments of the cDNAs produced by cutting a sample comprising a population of one or more cDNAs with a restriction endonuclease and isolating fragments whose restriction site is at the reference site.

3. A method according to claim 2, wherein the first sampling endonuclease binds to a first recognition site and cuts at the first sampling site at a predetermined displacement from the restriction site of the restriction endonuclease.

4. A method according to claim 3, wherein the first recognition site is provided in a first adaptor oligonucleotide which is hybridried to the restriction site of the isolated fragments.

5. A method according to claim 2, wherein the restriction endonuclease recognizes a 4 base pair binding site.

6. A method according to claim 2, wherein the second sub-fragments are sorted in step (b).

7. A method according to claim 1, wherein the first sampling endonuclease binds to the reference site and cuts at the first sampling site at a predetermined displacement from the reference site.

8. A method according to claim 1, wherein the first sampling endonuclease comprises a Type IIs endonuclease.

9. A method according to claim 1, wherein the second sampling endonuclease binds to a second recognition site and cuts at the second sampling site at a predetermined displacement from the first sampling site.

10. A method according to claim 9, wherein the second sampling endonuclease comprises a Type IIs endonuclease.

11. A method according to claim 9, wherein the second recognition site is provided in a second adaptor oligonucleotide which is hybridized to the first sticky end.

12. A method according to claim 1, wherein the tails of the cDNAs or fragments thereof are bound to a solid phase matrix.

13. A method according to claim 1, wherein the aggregate length of the first and second sticky end sequences of each sub-fragment is 8.

14. A method according to claim 13, wherein the length of each sticky end is 4.

15. A method according to claim 1, wherein the step (b) of sorting the sub-fragments comprises dividing the sub-fragments into an array of samples, each sample in a separate container; contacting the array of samples with an array of solid phase affinity matrices, each solid phase affinity matrix bearing a unique base sequence of the same predetermined length as the first sticky end, so that each sample is contacted with one of the possible base sequences and the array of samples is contacted with all possible base sequences of that predetermined length for hybridization to occur only between each unique base sequence and first sticky end complementary with one another; and washing unhybridized material from the containers.

16. A method according to claim 1, wherein the step (d) of determining each second sticky end sequence comprises isolating the further sub-fragments from step (c) and contacting the further sub-fragments with an array of adaptor oligonucleotides in a cycle, each adaptor oligonucleotide bearing a label and a unique base sequence of the same predetermined length as the second sticky end, the array containing all possible base sequences of that predetermined length; wherein the cycle comprises sequentially contacting each adaptor oligonucleotide of the array with each sub-population of isolated sub-fragments under hybridization conditions, removing any unhybridized adaptor oligonucleotide and determining the presence of any hybridized adaptor oligonucleotide by detection of the label, then repeating the cycle, until all of the adaptors in the array have been tested.

17. A method according to claim 1, wherein the step (b) of sorting the sub-fragments comprises (i) binding the sub-fragments to a hybridization array comprising an array of oligonucleotide sets, each set bearing a unique base sequence of the same predetermined length as the first sticky end and identifiable by location in the array, all possible base sequences of that predetermined length being present in the array, so that each sub-population bearing its unique first sticky end is hybridized at an identifiable location in the array; and (ii) determining the location to identify the first sticky end sequence.

18. A method according to claim 1, wherein the sub-fragments cut in step (c) are those bound to the hybridization array so that the further sub-fragments generated thereby remain bound to the hybridization array; and wherein the step (d) of determining each second sticky end sequence comprises contacting the further sub-fragments under hybridization conditions with an array of adaptor oligonucleotides, each adaptor oligonucleotide bearing a label and a unique base sequence of the same predetermined length as the second sticky end, the array containing all possible base sequences of that predetermined length, removing any unhybridized adaptor oligonucleotide, and determining the location of any hybridized adaptor oligonucleotide by detection of the label.

19. A method for identifying cDNA in a sample, which comprises characterizing cDNA in accordance with a method according to any one of the preceding claims, comparing the sequences and relative positions of the reference site and first and second sticky ends obtained thereby with the sequences and relative positions of the reference site and first and second sticky ends of known cDNAs in order to identify each CDNA in the sample.

20. A method for assaying for one or more specific cDNAs in a sample, which comprises performing a method according to claim 1, wherein the reference site is predetermined, each first sticky end sequence in sorting step (b) is a predetermined first sticky end sequence, each second sticky sequence in step (d) is determined by assaying for a predetermined second sticky end sequence, and the relative positions of the reference site and predetermined first and second sticky ends characterize the or each specific cDNA.

21. A method according to claim 20, wherein the reference site and first and second sticky end sequences are predetermined by selecting corresponding sequences from one or more known target cDNAs.

* * * * *

SEQUENCE LISTING (1) GENERAL INFORMATION:

(iii) NUMBER OF SEQUENCES: 41

(2) INFORMATION FOR SEQ ID NO: 1:

(i) SEQUENCE CHARACTERISTICS:
       (A) LENGTH: 254 base pairs
       (B) TYPE: nucleic acid
       (C) STRANDEDNESS: unknown
       (D) TOPOLOGY: unknown (ii) MOLECULE TYPE: DNA (genomic)

(xi) SEQUENCE DESCRIPTION: SEQ ID NO: 1:

```
CCAAAGCTGG GAGAGAACAG AATGCCTTGG TTTTCTGCTG CAGATCTTCC AGGACCACCC      60

ACTACAGAAG ACTTATAACT ACAACGTGTT GATGGTGCCC AAACCTCAGG GCCCCCTGCC     120

CAACACAGCC CTCCTCTCCC TTGTGCTCAT GGCCGGTACC TTCTTCTTTG CCATGATGCT     180

GCGCAAGTTC AAGAACAGCT CCTATTTCCC TGGCAAGTCA GCATACCCTC CTCGCCTGTC     240

CTTGCCAACA CTGC                                                      254
```

(2) INFORMATION FOR SEQ ID NO: 2:

(i) SEQUENCE CHARACTERISTICS:
       (A) LENGTH: 270 base pairs
       (B) TYPE: nucleic acid
       (C) STRANDEDNESS: unknown
       (D) TOPOLOGY: unknown (ii) MOLECULE TYPE: DNA (genomic)

(xi) SEQUENCE DESCRIPTION: SEQ ID NO: 2:

```
CTGGGAGAAT GCCAGGGAAA GGTCTCTGCC TCCCACCCTC CCAGGCCCAG CCCCCACCCT      60

GTCTCTCACG TGGTGATCTG AGACTCCAGG AATATGAGGA TGAAGACCAG CAGAGCAGGC     120

AGGGCGGAGG CAAAATCATC CAGATGGGAA ACTCGGAACG CAAGCCCAGT GGGTGGATGA     180

CCCAGCCCCG GGCTGAGGAG TTGACACCTT GAAGCCATCA GGCACCGAGA GTTTCTGTGG     240

GAGGGGGTAG CAGGTAAGAA TGCCAAGGGC                                      270
```

(2) INFORMATION FOR SEQ ID NO: 3:

(i) SEQUENCE CHARACTERISTICS:
       (A) LENGTH: 253 base pairs
       (B) TYPE: nucleic acid
       (C) STRANDEDNESS: unknown
       (D) TOPOLOGY: unknown (ii) MOLECULE TYPE: DNA (genomic)

(xi) SEQUENCE DESCRIPTION: SEQ ID NO: 3:

```
GTGATAGGCA CTGACCCCAG CCTCCGCCTG CAGGTGAAGA CCTGGCGCAT GCACTTATTC      60

ACGGGCATCC AGATCATCTG CCTGGCAGTG CTGTGGGTGG TGAAGTCCAC GCCGGCCTCC     120

CTGGCCCTGC CCTTCGTCCT CATCCTCACT GTGCCGCTGC GGCGCGTCCT GCTGCCGCTC     180

ATCTTCAGGA ACGTGGAGCT TCAGTGTGTT GAGTGGCTGC CTGGGCCTGG GGCACAAGAG     240

CTGGGAGCAT GCG                                                       253
```

(2) INFORMATION FOR SEQ ID NO: 4:

(i) SEQUENCE CHARACTERISTICS:
    (A) LENGTH: 30 base pairs
    (B) TYPE: nucleic acid
    (C) STRANDEDNESS: double
    (D) TOPOLOGY: unknown (ii) MOLECULE TYPE: DNA (genomic)

(xi) SEQUENCE DESCRIPTION: SEQ ID NO: 4:

TTCCAGGACC ACCCTAGAAG GTCCTGGTGG                                            30

(2) INFORMATION FOR SEQ ID NO: 5:

(i) SEQUENCE CHARACTERISTICS:
        (A) LENGTH: 38 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 5:

TGAGACTCCA GGAATATCTA GACTCTGAGG TCCTTATA                                   38

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 6:

ATCTGCCTGG CAGCTAGTAG ACGGACCGTC                                            30

(2) INFORMATION FOR SEQ ID NO: 7:

(i) SEQUENCE CHARACTERISTICS:
        (A) LENGTH: 44 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 7:

CTAGAGGACG ATCGAGGATG GATCTCCTGC TAGCTCCTAC GATC                            44

(2) INFORMATION FOR SEQ ID NO: 8:

(i) SEQUENCE CHARACTERISTICS:
        (A) LENGTH: 74 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 8:

CTAGAGGACG ATCGAGGATG GATCTTCCAG GACCACCGAT CTCCTGCTAG CTCCTACCTA           60

GAAGGTCCTG GTGG                                                            74

(2) INFORMATION FOR SEQ ID NO: 9:

(i) SEQUENCE CHARACTERISTICS:
        (A) LENGTH: 82 base pairs

```
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 9:

CTAGAGGACG ATCGAGGATG GATCTGAGAC TCCAGGAATA TGATCTCCTG CTAGCTCCTA      60

CCTAGACTCT GAGGTCCTTA TA                                              82

(2) INFORMATION FOR SEQ ID NO: 10:

(i) SEQUENCE CHARACTERISTICS:
        (A) LENGTH: 74 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 10:

CTAGAGGACG ATCGAGGATG GATCATCTGC CTGGCAGGAT CTCCTGCTAG CTCCTACCTA      60

GTAGACGGAC CGTC                                                       74

(2) INFORMATION FOR SEQ ID NO: 11:

(i) SEQUENCE CHARACTERISTICS:
        (A) LENGTH: 62 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 11:

CTAGAGGACG ATCGAGGATG GATCTTCCAG ATCTCCTGCT AGCTCCTACC TAGAAGGTCC      60

TG                                                                    62

(2) INFORMATION FOR SEQ ID NO: 12:

(i) SEQUENCE CHARACTERISTICS:
        (A) LENGTH: 62 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 12:

CTAGAGGACG ATCGAGGATG GATCTGAGAG ATCTCCTGCT AGCTCCTACC TAGACTCTGA      60

GG                                                                    62

(2) INFORMATION FOR SEQ ID NO: 13:

(i) SEQUENCE CHARACTERISTICS:
        (A) LENGTH: 62 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 13:

CTAGAGGACG ATCGAGGATG GATCATCTGG ATCTCCTGCT AGCTCCTACC TAGTAGACGG      60

AC                                                                    62
```

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 14:

GCAGCAGACG TCGTCTCAGG                                               20

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 15:

GCAGCAGACG TCGTCTCCTC                                               20

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 16:

GCAGCAGACG TCGTCTGTCC                                               20

(2) INFORMATION FOR SEQ ID NO: 17:

(i) SEQUENCE CHARACTERISTICS:
        (A) LENGTH: 82 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 17:

GCAGCAGAGT CCTGGAAGAT CCATCCAGCT AGCAGGAGAT CCGTCGTCTC AGGACCTTCT     60

AGGTAGGTCG ATCGTCCTCT AG                                      82

(2) INFORMATION FOR SEQ ID NO: 18:

(i) SEQUENCE CHARACTERISTICS:
        (A) LENGTH: 82 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 18:

GCAGCAGAGG AGTCTCAGAT CCATCCAGCT AGCAGGAGAT CCGTCGTCTC CTCAGAGTCT     60

AGGTAGGTCG ATCGTCCTCT AG                                      82

(2) INFORMATION FOR SEQ ID NO: 19:

(i) SEQUENCE CHARACTERISTICS:
        (A) LENGTH: 82 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 19:

```
GCAGCAGACA GGCAGATGAT CCATCCAGCT AGCAGGAGAT CCGTCGTCTG TCCGTCTACT      60

AGGTAGGTCG ATCGTCCTCT AG                                               82
```

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 20:

```
GCAGCAGAGT CCTCGTCGTC TCAGGACCTT                                       30
```

(2) INFORMATION FOR SEQ ID NO: 21:

(i) SEQUENCE CHARACTERISTICS:
        (A) LENGTH: 30 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 21:

```
GCAGCAGAGG AGTCGTCGTC TCCTCAGAGT                                       30
```

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 22:

```
GCAGCAGACA GGCCGTCGTC TGTCCGTCTA                                       30
```

(2) INFORMATION FOR SEQ ID NO: 23:

(i) SEQUENCE CHARACTERISTICS:
        (A) LENGTH: 34 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 23:

```
GGAAGATCCT GGACAGTTGC TAGGACCTGT CAAC                                  34
```

(2) INFORMATION FOR SEQ ID NO: 24:

(i) SEQUENCE CHARACTERISTICS:
        (A) LENGTH: 34 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 24:

CTCAGATCCT GGACAGTTGC TAGGACCTGT CAAC                    34

(2) INFORMATION FOR SEQ ID NO: 25:

(i) SEQUENCE CHARACTERISTICS:
        (A) LENGTH: 34 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 25:

AGATGATCCT GGACAGTTGC TAGGACCTGT CAAC                    34

(2) INFORMATION FOR SEQ ID NO: 26:

(i) SEQUENCE CHARACTERISTICS:
        (A) LENGTH: 44 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 26:

CTAGAGGACG ATCGAGGATG GATCTCCTGC TAGCTCCTAC CTAG          44

(2) INFORMATION FOR SEQ ID NO: 27:

(i) SEQUENCE CHARACTERISTICS:
        (A) LENGTH: 72 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 27:

CCCTAGACTA GAGGACCGAT CGAATCAGCA GCAGAGATCT GATCTCCTGG CTAGCTTAGT    60

CGTCGTCTCA GG                                                                   72

(2) INFORMATION FOR SEQ ID NO: 28:

(i) SEQUENCE CHARACTERISTICS:
        (A) LENGTH: 72 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 28:

CCCTAGACTA GAGGACCGAT CGAATCAGCA GCAGAGATCT GATCTCCTGG CTAGCTTAGT    60

CGTCGTCTCC TC                                                                   72

(2) INFORMATION FOR SEQ ID NO: 29:

(i) SEQUENCE CHARACTERISTICS:
        (A) LENGTH: 72 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 29:

```
CCCTAGACTA GAGGACCGAT CGAATCAGCA GCAGAGATCT GATCTCCTGG CTAGCTTAGT    60

CGTCGTCTGT CC                                                        72
```

(2) INFORMATION FOR SEQ ID NO: 30:

(i) SEQUENCE CHARACTERISTICS:
        (A) LENGTH: 34 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 30:

```
CAACTGTCCA GGATCGTTGA CAGGTCCTAG AAGG                                34
```

(2) INFORMATION FOR SEQ ID NO: 31:

(i) SEQUENCE CHARACTERISTICS:
        (A) LENGTH: 34 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 31:

```
CAACTGTCCA GGATCGTTGA CAGGTCCTAG ACTC                                34
```

(2) INFORMATION FOR SEQ ID NO: 32:

(i) SEQUENCE CHARACTERISTICS:
        (A) LENGTH: 34 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 32:

```
CAACTGTCCA GGATCGTTGA CAGGTCCTAG TAGA                                34
```

(2) INFORMATION FOR SEQ ID NO: 33:

(i) SEQUENCE CHARACTERISTICS:
        (A) LENGTH: 92 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 33:

```
GGTCACTTAG ATCGATCCAT GAGGATGCTT CATTCTGATT CAGTCCCCAG TGAATCTAGC    60

TAGGTACTCC TACGAAGTAA GACTAAGTCA GG                                  92
```

(2) INFORMATION FOR SEQ ID NO: 34:

(i) SEQUENCE CHARACTERISTICS:
        (A) LENGTH: 64 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 34:

```
GCATCTGGAG TCTACAGTCG TCTATTGACG CGTAGACCTC AGATGTCAGC AGATAACTGC      60

CGGC                                                                   64
```

(2) INFORMATION FOR SEQ ID NO: 35:

(i) SEQUENCE CHARACTERISTICS:
        (A) LENGTH: 36 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 35:

```
GCATCAGGAT GTACAGCGTA GTCCTACATG TCGCCA                                36
```

(2) INFORMATION FOR SEQ ID NO: 36:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 36:

```
GTATTTTCCA GCCCAAGCCA AAGCTGG                                          27
```

(2) INFORMATION FOR SEQ ID NO: 37:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 37:

```
GCAGTGTTGG CAAGGACAGG C                                                21
```

(2) INFORMATION FOR SEQ ID NO: 38:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 38:

```
GCCCTTGGCA TTCTTACCTG C                                                21
```

(2) INFORMATION FOR SEQ ID NO: 39:

-continued

```
    (i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 39:

CTGGGAGAAT GCCAGGGAAA GG                                            22

(2) INFORMATION FOR SEQ ID NO: 40:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 40:

GTGATAGGCA CTGACCCCAG                                               20

(2) INFORMATION FOR SEQ ID NO: 41:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 41:

CGCATGCTCC CAGCTCTTGT GC                                            22
```